United States Patent
Naing et al.

(10) Patent No.: US 9,326,731 B2
(45) Date of Patent: May 3, 2016

(54) METHOD OF MEASURING AN ARTEFACT REMOVED PHOTOPLETHYSMOGRAPHIC (PPG) SIGNAL AND A MEASUREMENT SYSTEM

(75) Inventors: Nyan Myo Naing, Singapore (SG); Md Irwan Bin Md Kassim, Singapore (SG); Mohamad Sulhede Bin Samsudin, Singapore (SG); Visit Thaveeprungsriporn, Singapore (SG)

(73) Assignee: NITTO DENKO CORPORATION (JP)

( * ) Notice: Subject to any disclaimer, the term of this patent is extended or adjusted under 35 U.S.C. 154(b) by 0 days.

(21) Appl. No.: 14/006,265

(22) PCT Filed: Mar. 26, 2012

(86) PCT No.: PCT/SG2012/000104
§ 371 (c)(1),
(2), (4) Date: Nov. 8, 2013

(87) PCT Pub. No.: WO2012/134395
PCT Pub. Date: Oct. 4, 2012

(65) Prior Publication Data
US 2014/0058272 A1    Feb. 27, 2014

(30) Foreign Application Priority Data
Mar. 25, 2011 (SG) .................................. 201102122

(51) Int. Cl.
*A61B 5/1455* (2006.01)
*A61B 5/00* (2006.01)
(Continued)

(52) U.S. Cl.
CPC ............. *A61B 5/7203* (2013.01); *A61B 5/0261* (2013.01); *A61B 5/0295* (2013.01); *A61B 5/02405* (2013.01); *A61B 5/14551* (2013.01); *A61B 5/725* (2013.01); *A61B 5/7207* (2013.01)

(58) Field of Classification Search
CPC ............. A61B 5/14551; A61B 5/0261; A61B 5/1455; A61B 5/72; A61B 5/7203; A61B 5/14552
USPC ......... 600/310, 322, 323, 326, 336, 340, 344, 600/473, 476, 479; 356/41
See application file for complete search history.

(56) References Cited

U.S. PATENT DOCUMENTS

| 4,911,167 A | * | 3/1990 | Corenman et al. ............ 600/324 |
| 5,632,272 A | | 5/1997 | Diab et al. |

(Continued)

FOREIGN PATENT DOCUMENTS

| WO | 94/03102 A1 | 2/1994 |
| WO | 96/12435 A2 | 5/1996 |
| WO | 2011/026986 A1 | 3/2011 |

OTHER PUBLICATIONS

Julian M. Goldman, MD, et al., "Masimo Signal Extraction Pulse Oximetry", Journal of Clinical Monitoring and Computing, vol. 16, pp. 475-483, 2000, Kluwer Academic Publishers, The Netherlands.

(Continued)

*Primary Examiner* — Tse Chen
*Assistant Examiner* — Chu Chuan (JJ) Liu
(74) *Attorney, Agent, or Firm* — Volpe and Koenig, P.C.

(57) ABSTRACT

A method of measuring an artifact removed photoplethysmographic (PPG) signal and a measurement system for measuring an artifact removed photoplethysmographic (PPG) signal are provided. The method comprises obtaining a first set of PPG signals from a plurality of detectors at respective measurement sites using a first illumination; obtaining a second set of PPG signals from the plurality of detectors using a second illumination; obtaining at least two pairs of PPG signals, each pair comprising one PPG signal from the first set and one PPG signal from the second set, and for each pair, computing an artifact reference signal to obtain a candidate PPG signal; and choosing one of the candidate PPG signals as the artifact removed PPG signal.

21 Claims, 24 Drawing Sheets

(51) Int. Cl.
*A61B 5/024* (2006.01)
*A61B 5/0295* (2006.01)
*A61B 5/026* (2006.01)

(56) References Cited

U.S. PATENT DOCUMENTS

| | | | |
|---|---|---|---|
| 7,020,507 B2* | 3/2006 | Scharf et al. | 600/336 |
| 2006/0200015 A1* | 9/2006 | Baker, Jr. | 600/323 |
| 2008/0019218 A1 | 1/2008 | Klopfenstein et al. | |
| 2009/0143655 A1* | 6/2009 | Shani | 600/323 |
| 2012/0046532 A1* | 2/2012 | Chang et al. | 600/324 |

OTHER PUBLICATIONS

Yong-Sheng Yan et al., "An Efficient Motion-Resistant Method for Wearable Pulse Oximeter", IEEE Transactions on Information Technology in Biomedicine, vol. 12, No. 3, pp. 399-405, May 2008.

Rhee, Sokwoo et al.; Artifact-Resistant Power-Efficient Design of Finger-Ring Plethysmographic Sensors, IEEE Transactions on Biomedical Engineering, Jul. 2001, pp. 795-805, vol. 48, No. 7.

* cited by examiner

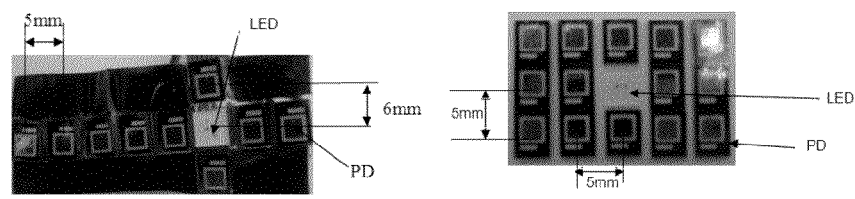
Figure 23                    Figure 24

METHOD OF MEASURING AN ARTEFACT REMOVED PHOTOPLETHYSMOGRAPHIC (PPG) SIGNAL AND A MEASUREMENT SYSTEM

FIELD OF INVENTION

The present invention relates broadly to a method of measuring an artefact removed photoplethysmographic (PPG) signal and a measurement system.

BACKGROUND

Photoplythesmography has been used as a non-invasive measurement of vital signs. Vital signs can include blood oxygen saturation (SpO2), heart rate (HR) and heart rate variation (HRV). Photoplythesmographic measurement is based on the knowledge that haemoglobin and oxy-haemoglobin absorb varying degrees of light at different wavelengths. A dual-wavelength illumination (i.e. using a wavelength of about 600 nm of a red light source and a wavelength of about 900 nm of an infrared light source) of arterial blood can result in an absorption contrast based on the proportion of haemoglobin that is chemically combined with oxygen. Pulse oximeters (for measurement of oxygen saturation in blood) can obtain and measure the optical absorption contrast between blood and other anatomical constituents. In contrast to the other constituents, pulsating arterial blood typically induce dynamics into the absorption characteristics of well-perfused peripheral sites. Well-perfused sites refer to areas where the blood oxygen saturation level is high. The dynamics referred to are termed as photoplethysmographic (PPG) signals or blood volume pulses (BVP). SpO2 can be derived from the absorption contrast from dual wavelength illumination. HR and HRV can be derived from PPG signals.

However, a significant factor limiting both practical accuracy and general applicability of pulse oximetry is poor PPG signal-to-noise ratio (SNR) that is typically caused by low-perfusion states or artefacts/artefact corruption. Artefact corruption arises mostly from voluntary or involuntary subject movement (i.e. motion artefact) and typically leads to interpretation errors for pulse oximetry. The interpretation errors constitute a significant proportion of clinical false alarm conditions.

There have been attempts made to improve the accuracy of a pulse oximeter where a subject is moving. These are discussed in Goldman et. al., signal extraction pulse oximetry, Journal of Clinical Monitoring and Computing, 16, 475-483, 2000 and Sokwoo et. al., Artifact-resistant powerefficient design of finger-ring plethysmographic sensors, IEEE Transactions on Biomedical Engineering, 48(7), 795-805, 2001. One typical method is based on an independent measure of motion. For example, one or more transducers (e.g., accelerometer or optical sensors) are employed to record the user's motion. By assuming that the (motion) artefact is a linear addition to the PPG signal obtained, the original signal can be reconstructed from the corrupted signal. The reconstruction is discussed in PCT publications WO 96/12435 and WO 94/03102.

Another approach to improve accuracy is an implementation of a motion-resistant algorithm termed as discrete saturation transform (DST). This algorithm is able to detect SpO2 during low perfusion and during motion using an adaptive filter, based on a model derived from the Beer-Lambert law. The law is discussed in Goldman et. al. and in U.S. Pat. No. 5,632,272. A number of studies have shown that DST has a significantly lower failure rate and a lower false positive alarm rate than conventional techniques. Refer to Yong-Sheng Yan et. al., An Efficient Motion-Resistant Method for Wearable Pulse Oximeter, IEEE Transactions on Information Technology in Biomedicine, 12(3), 399-405, 2008. As discussed in U.S. Pat. No. 5,632,272, the SpO2 measurement model based on DST includes measuring the true PPG signal and the artefact signal. Based on the relationships of PPG signals (inclusive of noise) obtained from red and infrared red light sources, a coefficient is chosen from the energy spectrum of the adaptive filter outputs by scanning through a range of possible coefficients. Local maximums in the obtained energy spectrum can then provide corresponding saturation ($SpO_2$ and $SvO_2$) values.

The method using DTS recognised that, given that the human anatomy has different layers of constituents, when perturbation such as external force or human movement occurs, each layer may be affected by the perturbation differently when compared to other layers. The method using DTS considers the different layers of constituents and different behaviours at perturbation that cause the secondary signal component, i.e., motion artefact, at the measured PPG signal.

However, the method using DST only allows the measurement of the PPG signal in a controlled environment e.g. in a hospital ward/operating theatre. In these controlled environments, the patient is the subject of the measurement, and undergoes only minor movements. On the other hand, in a free environment, where the subject of the measurement is an active individual, the extent of movement of the subject is typically increased. This typically results in increased motion artefacts which are significantly difficult to remove from obtained PPG signals using current methods. This typically, leads to diminished accuracy in the measured parameters e.g. $SpO_2$, HR and HRV obtained from the PPG signals.

Hence, in view of the above, there exists a need for a method of measuring an artefact removed photoplethysmographic (PPG) signal and a measurement system that seek to address at least one of the above problems.

SUMMARY

In accordance with a first aspect of the present invention, there is provided a method of measuring an artefact removed photoplethysmographic (PPG) signal, the method comprising obtaining a first set of PPG signals from a plurality of detectors at respective measurement sites using a first illumination; obtaining a second set of PPG signals from the plurality of detectors using a second illumination; obtaining at least two pairs of PPG signals, each pair comprising one PPG signal from the first set and one PPG signal from the second set, and for each pair, computing an artefact reference signal to obtain a candidate PPG signal; and choosing one of the candidate PPG signals as the artefact removed PPG signal.

The step of computing an artefact reference signal may comprise using a vector subspace approach whereby, for the pairs of PPG signals, artefact reference signals between $$0 \sim \frac{\pi}{2}$$

are considered for further computation.

The considered artefact reference signals may be separated into a plurality of subspaces, wherein from each of said plurality of subspaces, a selected artefact reference signal may be applied to a filter with one of said one PPG signal from the first set and one PPG signal from the second set to determine a subspace for analysis.

The step of choosing one of the candidate PPG signals may comprise using one or more parameters to compare the candidate PPG signals.

The parameters may comprise an averaged standard deviation of maximum peak points and minimum peak points of each candidate PPG signal.

The parameters may comprise a cross-correlation of two separated segments of each candidate PPG signal.

The method may further comprise applying a force at the plurality of detectors such that signal amplitudes of the first set of PPG signals and/or the second set of PPG signals are maximum.

The method may comprise computing an area under curve measurement using waveforms of the PPG signals to determine whether the signal amplitudes are maximum.

The computing an area under curve measurement may comprise sampling each waveform and filtering each sample, further wherein the area under curve measurement is a summation of absolute values of the filtered samples.

The method may further comprise providing the first and second illumination using a light emitting diode.

The light emitting diode may be positioned such that motion artefacts are minimized in the first set of PPG signals and/or the second set of PPG signals.

The first illumination may be red light and the second illumination may be infrared red light.

In accordance with a second aspect of the present invention, there is provided a measurement system for measuring an artefact removed photoplethysmographic (PPG) signal, the system comprising a measurement device comprising a plurality of detectors at respective measurement sites for obtaining a first set of PPG signals using a first illumination and for obtaining a second set of PPG signals using a second illumination; a computation unit for obtaining at least two pairs of PPG signals, each pair comprising one PPG signal from the first set and one PPG signal from the second set, and the computation unit being capable of, for each pair, computing an artefact reference signal to obtain a candidate PPG signal; and the computation unit being capable of choosing one of the candidate PPG signals as the artefact removed PPG signal.

For computing an artefact reference signal, the computation unit may be capable of using a vector subspace approach whereby, for the pairs of PPG signals, artefact reference signals between $$0 \sim \frac{\pi}{2}$$

are considered for further computation.

For the vector subspace approach, the computation unit may separate the considered artefact reference signals into a plurality of subspaces, and from each of said plurality of subspaces, the computation unit selects a selected artefact reference signal and applies the selected artefact reference signal to a filter with one of said one PPG signal from the first set and one PPG signal from the second set to determine a subspace for analysis.

For choosing one of the candidate PPG signals, the computation unit may be capable of using one or more parameters to compare the candidate PPG signals.

The parameters may comprise an averaged standard deviation of maximum peak points and minimum peak points of each candidate PPG signal.

The parameters may comprise a cross-correlation of two separated segments of each candidate PPG signal.

The system may further comprise a force application means for applying a force at the plurality of detectors such that signal amplitudes of the first set of PPG signals and/or the second set of PPG signals are maximum.

The computation unit may be capable of computing an area under curve measurement using waveforms of the PPG signals to determine whether the signal amplitudes are maximum.

For the computing an area under curve measurement, the computation unit may sample each waveform and may filter each sample, and further the computation unit may compute the area under curve measurement as a summation of absolute values of the filtered samples.

The system may further comprise an automatic sizing component to automatically size the measurement device for application to a subject, the automatic sizing component functioning as the force application means.

The system may further comprise a light emitting diode for providing the first and second illumination.

The light emitting diode may be positioned such that motion artefacts are minimized in the first set of PPG signals and/or the second set of PPG signals.

The first illumination may be red light and the second illumination may be infrared red light.

The measurement device and the computation unit may each comprise a wireless transceiver to facilitate communication using a wireless communication protocol.

In accordance with a third aspect of the present invention, there is provided a computer readable data storage medium having stored thereon computer code means for instructing a processor of a measurement system for measuring an artefact removed photoplethysmographic (PPG) signal to execute a method of the first aspect.

BRIEF DESCRIPTION OF THE DRAWINGS

Embodiments of the invention will be better understood and readily apparent to one of ordinary skill in the art from the following written description, by way of example only, and in conjunction with the drawings, in which:

FIG. 23 shows a picture of a nine-PD array in an example embodiment.

FIG. 24 shows a picture of a fourteen-PD array in an example embodiment.

DETAILED DESCRIPTION

Figure 1:
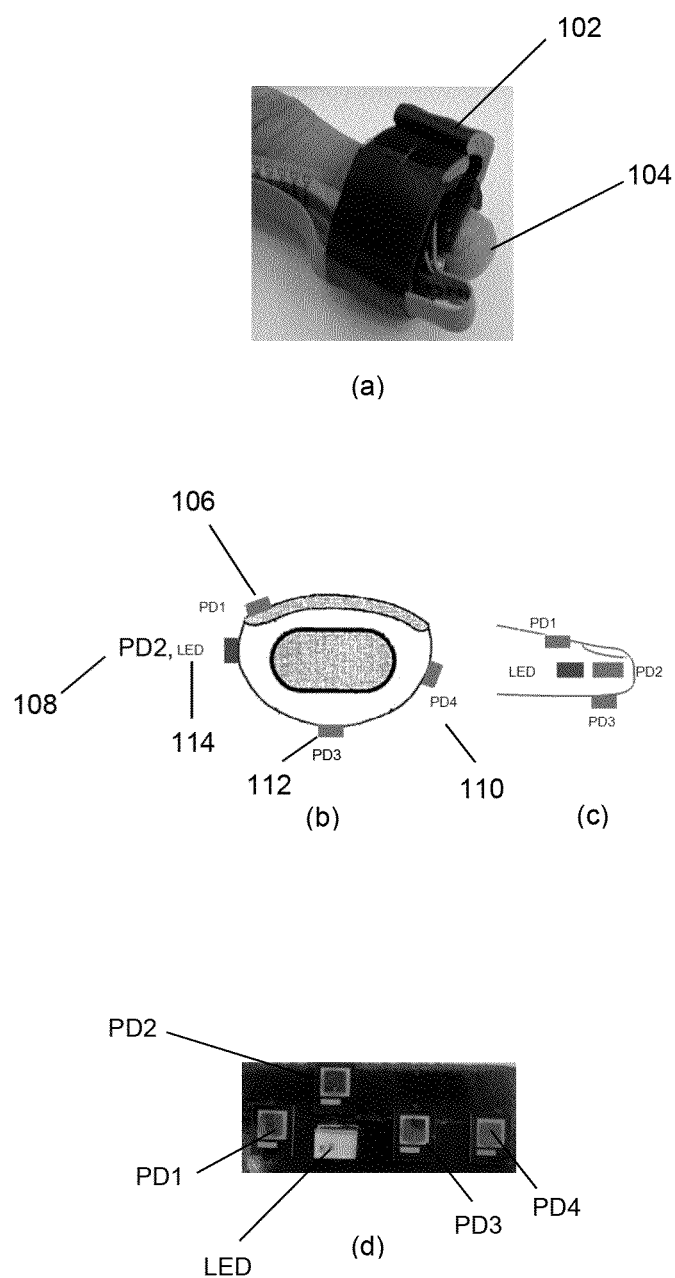
FIG. 1(a) is a picture of a measurement device in an example embodiment.
FIG. 1(b) is a schematic front view of FIG. 1(a).
FIG. 1(c) is a schematic side view of FIG. 1(a).
FIG. 1(d) shows a laid-open view of a measurement device of FIG. 1(a).

The inventors have recognised that measurement locations/sites (e.g. using photo-detectors) experience different perturbations, resulting in measured photoplethysmographic (PPG) signals having different amounts of artefacts. In an example embodiment, by using an array of photo-detectors, it can be observed that while PPG signals obtained from one measurement site contain significant motion artefacts, PPG signals obtained at a different measurement site may have lesser motion artefacts.

Furthermore, the inventors have recognised that the pressure applied at a measurement site and the positioning of the illumination source for PPG measurement e.g. a light emitting diode (LED) can also contribute to minimising motion artefacts in a measured PPG signal.

Therefore, in the following description, there are two broad steps taken in motion artefact removal in a PPG signal. The two steps are motion artefact minimization (e.g. by using a photo-detector (PD) array, and/or by applying optimum pressure and/or positioning of a LED on a finger), and motion artefact removal using an adaptive filter.

Furthermore, the inventors have recognised that by increasing the number of PDs, computations are correspondingly increased. Therefore, an algorithm comprising a vector subspace approach is also provided to reduce a significant amount of data processing.

Some portions of the description which follows are explicitly or implicitly presented in terms of algorithms and functional or symbolic representations of operations on data within a computer memory. These algorithmic descriptions and functional or symbolic representations are the means used by those skilled in the data processing arts to convey most effectively the substance of their work to others skilled in the art. An algorithm is here, and generally, conceived to be a self-consistent sequence of steps leading to a desired result. The steps are those requiring physical manipulations of physical quantities, such as electrical, magnetic or optical signals capable of being stored, transferred, combined, compared, and otherwise manipulated.

Unless specifically stated otherwise, and as apparent from the following, it will be appreciated that throughout the present specification, discussions utilizing terms such as "scanning", "calculating", "determining", "replacing", "generating", "initializing", "outputting", or the like, refer to the action and processes of a computer system, or similar electronic device, that manipulates and transforms data represented as physical quantities within the computer system into other data similarly represented as physical quantities within the computer system or other information storage, transmission or display devices.

The present specification also discloses apparatus for performing the operations of the methods. Such apparatus may be specially constructed for the required purposes, or may comprise a general purpose computing device or other device selectively activated or reconfigured by a computer program stored in the device. The algorithms and displays presented herein are not inherently related to any particular computer or other apparatus. Various general purpose machines may be used with programs in accordance with the teachings herein. Alternatively, the construction of more specialized apparatus to perform the required method steps may be appropriate.

In addition, the present specification also implicitly discloses a computer program, in that it would be apparent to the person skilled in the art that the individual steps of the method described herein may be put into effect by computer code. The computer program is not intended to be limited to any particular programming language and implementation thereof. It will be appreciated that a variety of programming languages and coding thereof may be used to implement the teachings of the disclosure contained herein. Moreover, the computer program is not intended to be limited to any particular control flow. There are many other variants of the computer program, which can use different control flows without departing from the spirit or scope of the invention.

Furthermore, one or more of the steps of the computer program may be performed in parallel rather than sequentially. Such a computer program may be stored on any computer readable medium. The computer readable medium may include storage devices such as magnetic or optical disks, memory chips, or other storage devices suitable for interfacing with a general purpose computing device. The computer readable medium may also include a hard-wired medium such as exemplified in the Internet system, or wireless medium such as exemplified in the GSM mobile telephone system. The computer program when loaded and executed on such a general-purpose computing device effectively results in an apparatus that implements the steps of the preferred method.

The invention may also be implemented as hardware modules. More particular, in the hardware sense, a module is a functional hardware unit designed for use with other components or modules. For example, a module may be implemented using discrete electronic components, or it can form a portion of an entire electronic circuit such as an Application Specific Integrated Circuit (ASIC). Numerous other possibilities exist. Those skilled in the art will appreciate that the system can also be implemented as a combination of hardware and software modules.

FIG. 1(a) is a picture of a measurement device in an example embodiment. The measurement device 102 is attached to e.g. an index finger 104. In the example embodiment, the measurement device 102 comprises a photo-detector (PD) array having four PDs.

FIG. 1(b) is a schematic front view of FIG. 1(a). FIG. 1(c) is a schematic side view of FIG. 1(a). FIG. 1(d) shows a laid-open view of the measurement device 102. In use, the measurement device 102 is wrapped around the finger 104. PD1 106 is disposed on top of the finger 104, PD2 108 is disposed at one side of the finger 104 with PD4 110 disposed on the other side of the finger 104, and PD3 112 is disposed on the bottom of the finger 104. An illumination source, i.e. an LED 114, is disposed adjacent the PD2 108.

Figure 2:
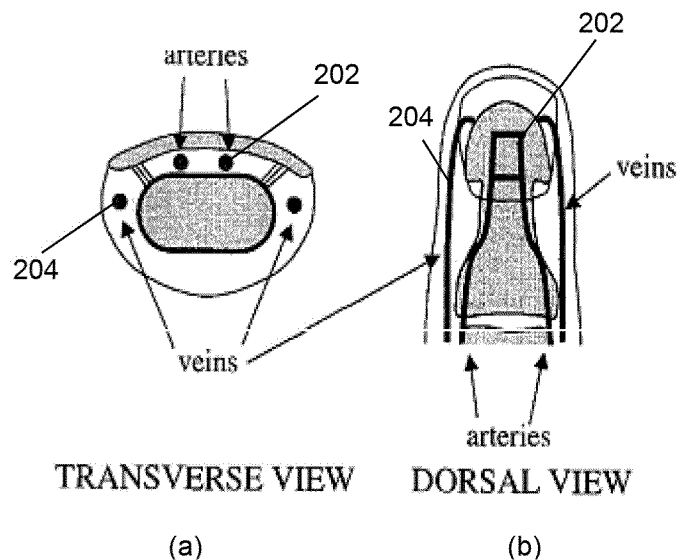
FIG. 2(a) shows a schematic transverse view of a finger.
FIG. 2(b) shows a schematic dorsal view of a finger.

FIG. 2(a) shows a schematic transverse view of a finger. FIG. 2(b) shows a schematic dorsal view of a finger. It is shown schematically that arteries e.g. 202 are disposed substantially on the top of the finger and veins e.g. 204 are disposed substantially by the sides of the finger.

Figure 3:
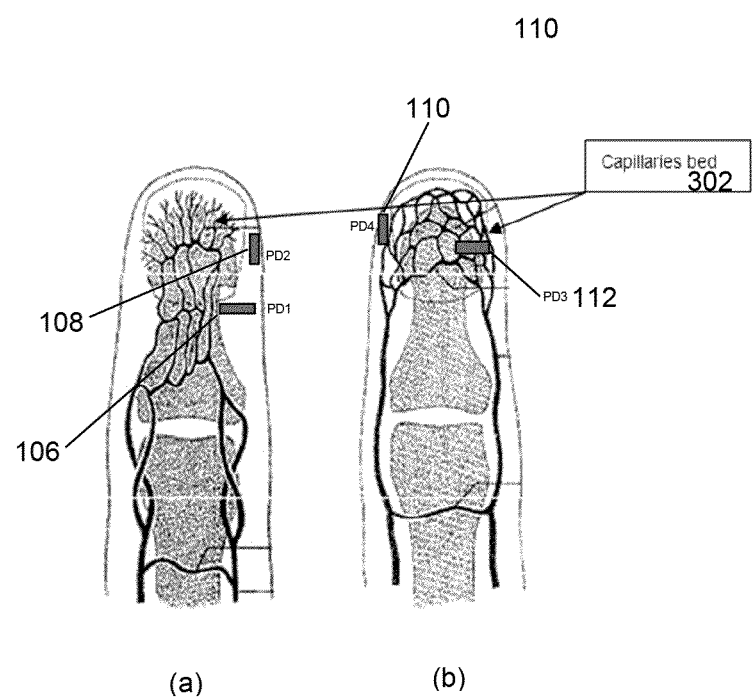
FIG. 3(a) is a schematic top view of FIG. 1(b).
FIG. 3(b) is a schematic bottom view of FIG. 1(b).

FIG. 3(a) is a schematic top view of FIG. 1(b). FIG. 3(b) is a schematic bottom view of FIG. 1(b). From the position of the PD array, PD1 106 is positioned to capture PPG data from the arteries e.g. 202 (FIG. 2) and PD2 108, PD3 112 and PD4 110 are respectively positioned to capture data from the capillaries bed 302. The inventors have recognised that arteries e.g. 202 (FIG. 2) can provide better PPG signals while the capillaries e.g. from the capillaries bed 302 provide better noise reference signals, i.e. PPG signals which are more affected by noise and containing motion artefacts.

In the example embodiment, the photo-detectors at the different measurement sites experience different perturbations, resulting in measured PPG signals having different amounts of artefacts. By using an array of photo-detectors, it can be observed that while PPG signals obtained from one measurement site contain significant motion artefacts, PPG signals obtained at a different measurement site may have lesser motion artefacts.

The following description describes motion artefact removal.

In the example embodiment, the LED 114 of FIG. 1 can provide a red light source or an infrared red light source.

Figure 4:
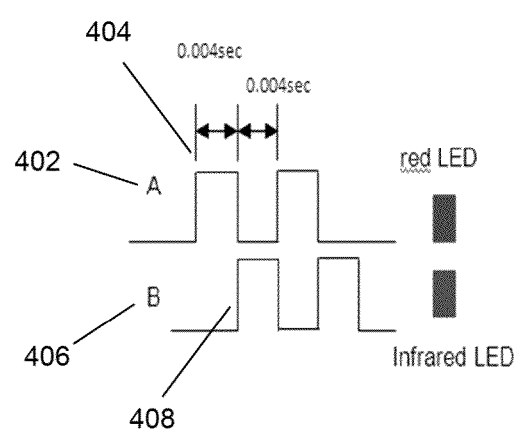
FIG. 4 shows timing signals for switching a light emitting diode into a red or infrared red light source in an example embodiment.

FIG. 4 shows respective timing signals for switching the LED 114 of FIG. 1 into a red or infrared red light source in the example embodiment. At condition A 402, at a first time interval 404, a high signal is sent to switch the LED 114 (FIG. 1) to become a red LED. At condition B 406, at the next time interval 408, a high signal is sent to switch the LED 114 (FIG. 1) to become an infrared red LED. The two time intervals 404 and 408 make up one cycle.

Thus, each PD1 to PD4, numerals 106,108,110,112 (FIG. 1) measures red (R) and infrared red (IR) PPG signals. Red PPG signals are collected during the time the LED 114 (FIG. 1) is a red light source and infrared PPG signals are collected during the time the LED 114 (FIG. 1) is an infrared red light source. Therefore, in one cycle, there are altogether four red PPG and four infrared red PPG signals collected. Using the red and infrared red PPG signals, sixteen pairs of red and infrared red PPG signals can be obtained for motion artefact removal.

Figure 5:
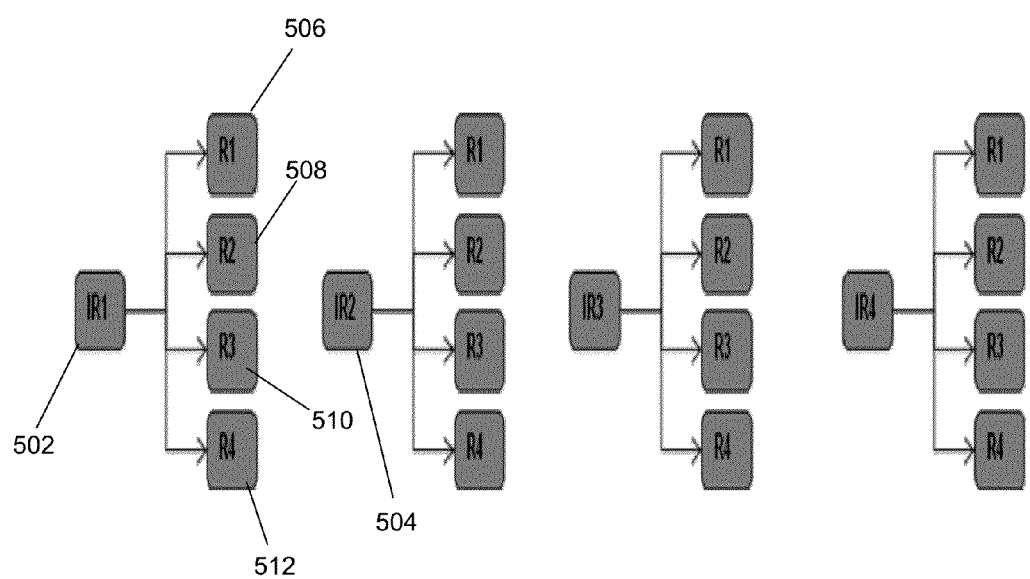
FIG. 5 is a schematic drawing showing sixteen pairs of red and infrared red photoplethysmographic (PPG) signals in an example embodiment.

FIG. 5 is a schematic drawing showing sixteen pairs of red and infrared red PPG signals in the example embodiment. IR1 502 denotes the infrared red PPG signal detected by PD1 106 (FIG. 1) and IR2 504 denotes the infrared red PPG signal detected by PD2 108 (FIG. 1). R1 506 denotes the red PPG signal detected by PD1 106 (FIG. 1); R2 508 denotes the red PPG signal detected by PD2 108 (FIG. 1); R3 510 denotes the red PPG signal detected by PD3 112 (FIG. 1); and R4 512 denotes the red PPG signal detected by PD4 110 (FIG. 1). IR1 502 forms four pairs of red and infrared red PPG signals with R1 506, R2 508, R3 510 and R4 512. Similarly, IR2 504 forms another four pairs of red and infrared red PPG signals with R1 506, R2 508, R3 510 and R4 512. With the four infrared red PPG signals, sixteen pairs of red and infrared red PPG signals can be obtained.

In motion artefact removal, an artefact reference (AR) is extracted using equation (1), where R is a red PPG signal and IR is an infrared red PPG signal from a pair.

$$\text{Artefact reference (AR)} = R - \text{ratio} * IR \quad (1)$$

The ratio is the optical density ratio related to oxygen saturation in which the artefact component is taken into consideration. The ratio is shown calculated according to equation (2).

$$\text{ratio} = \frac{R + N_1}{IR + N_2} \quad (2)$$

where $N_1$ and $N_2$ are non-arterial signals e.g. motion artefacts or noise.

By letting $S_1$ be a red PPG signal with a noise signal $N_1$ and $S_2$ be an infrared red PPG signal with a noise signal $N_2$, and using equation (1), the following is obtained.

$$S_1 = R + N_1 \quad (3)$$
$$S_2 = IR + N_2$$
$$S_1 - \text{ratio} * S_2 = R + N_1 - \text{ratio} * IR - \text{ratio} * N_2$$
$$\text{at } \text{ratio}_{opt}, R = \text{ratio}_{opt} * IR$$
$$\text{so } AR_{opt} = S_1 - \text{ratio}_{opt} * S_2 = N_1 - \text{ratio}_{opt} * N_2$$
$$\text{ratio}_{opt} = \frac{N_1 - S_1}{N_2 - S_2} = \frac{N_1'}{N_2'}$$

-continued $$ratio_{opt} = \frac{N'_1}{N'_2}$$

At equation (3), if the ratio is the correct ratio (ratio$_{opt}$), desired signals of red PPG and infrared red PPG are cancelled and only the undesired signal component remains.

Thus, in the example embodiment, if the correct ratio can be chosen, the AR signal has only the undesired signal component and can be used as a reference signal to remove artefacts from PPG signals.

Figure 6:
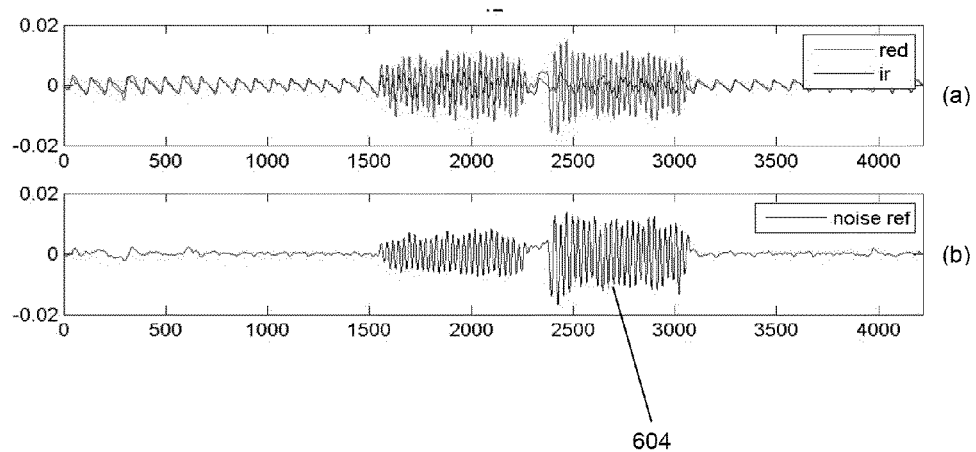
FIG. 6(a) is a graph showing a pair of red PPG signal and infrared red PPG signal including an artefact in an example embodiment.
FIG. 6(b) is a graph showing a noise/artefact reference signal extracted from FIG. 6(a) using a $ratio_{opt}$.

FIG. 6(a) is a graph showing a pair of red PPG signal and infrared red PPG signal including an artefact in the example embodiment. FIG. 6(b) is a graph showing a noise/artefact reference signal 604 extracted from FIG. 6(a) using ratio$_{opt}$. The graphs of FIGS. 6(a) and (b) are amplitude and sample (by time) graphs.

In determining the ratio$_{opt}$ at each pair of R and IR, a range of the ratio, e.g., 0:0.01:1, is considered, that is, from zero to 1 in steps of 0.01. Therefore, there can be 100 possible ratios and 100 possible AR signals. For 16 pairs of R and IR PPG signals, there are 16 pairs×100=1600 artefact reference (AR) signals. It has been recognised that a significant amount of computation is needed analyze all 1600 AR signals. In such a scenario, a vector subspace approach is used. With this approach, noise can be separated from the signals.

A subspace angle Ø is measured between an AR signal and an IR PPG signal using the equation (4).

$$\phi = a\cos(AR', IR) \quad (4)$$

In equation (4), AR is an artefact reference signal and a column vector. Therefore, $AR' = [a_1, a_2, a_3, \ldots, a_n]$. IR is an infrared red PPG signal and a column vector, i.e. $IR' = [y_1, y_2, y_3, \ldots, y_n]$.

If AR and IR have a high correlation, the angle is small and for an independent signal, the angle is $$\frac{\pi}{2}.$$

With that concept, only an AR signal between $$0 \sim \frac{\pi}{2}$$

is considered. Thereafter, a binary search approach is used to choose the optimum ratio (ratio$_{opt}$)

Figure 7:
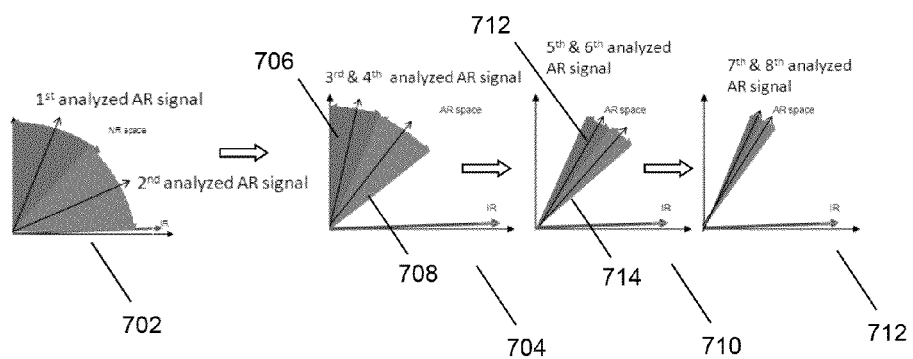
FIG. 7 schematically illustrates a binary search approach for obtaining $ratio_{opt}$ in a vector subspace in an example embodiment.

FIG. 7 schematically illustrates a binary search approach for ratio$_{opt}$ in a vector subspace in the example embodiment. By applying equation (1), there are 100 artefact references, i.e. $AR_{0:0.01:1} = R - ratio_{0:0.01:1} * IR$. A subspace angle Ø is measured between each AR signal and IR signal. There are approximately 50 AR signals that fall into the $$0 \sim \frac{\pi}{2}$$

vector space. Table 1 below tabulates the 50 AR signals in the considered vector space.

TABLE 1

| | |
|---|---|
| $AR_0$ | $[a_1, a_2, a_3, a_4, a_5, \ldots, a_n]$ where n is the length of the signal. |
| $AR_{0.01}$ | $[b_1, b_2, b_3, b_4, b_5, \ldots, b_n]$ |
| $AR_{0.02}$ | $[c_1, c_2, c_3, c_4, c_5, \ldots, c_n]$ |
| . | . |
| $AR_{0.125}$ | $[d_1, d_2, d_3, d_4, d_5, \ldots, d_n]$ First analyzed AR signal |
| . | . |
| $AR_{0.22}$ | $[e_1, e_2, e_3, e_4, e_5, \ldots, e_n]$ |
| $AR_{0.23}$ | $[f_1, f_2, f_3, f_4, f_5, \ldots, f_n]$ |
| $AR_{0.24}$ | $[g_1, g_2, g_3, g_4, g_5, \ldots, g_n]$ |
| $AR_{0.25}$ | $[h_1, h_2, h_3, h_4, h_5, \ldots, h_n]$ |
| $AR_{0.26}$ | $[i_1, i_2, i_3, i_4, i_5, \ldots, i_n]$ |
| $AR_{0.27}$ | $[j_1, j_2, j_3, j_4, j_5, \ldots, j_n]$ |
| . | . |
| $AR_{0.35}$ | $[k_1, k_2, k_3, k_4, k_5, \ldots, k_n]$ Second analyzed AR signal |
| . | . |
| $AR_{0.47}$ | $[l_1, l_2, l_3, l_4, l_5, \ldots, l_n]$ |
| $AR_{0.48}$ | $[m_1, m_2, m_3, m_4, m_5, \ldots, m_n]$ |
| $AR_{0.49}$ | $[n_1, n_2, n_3, n_4, n_5, \ldots, n_n]$ |

The vector space is separated into two subspaces, $S_{green}$ [from 0 to 0.24] and $S_{blue}$ [from 0.25 to 0.49]. $AR_{0.125}$ and $AR_{0.35}$ are selected from the two subspaces as a first analysis signal and a second analysis signal respectively. This is schematically shown at graph 702. $AR_{0.125}$ and $AR_{0.35}$ are selected from the two subspaces as these signals are approximately at the centre of their respective subspaces. $AR_{0.125}$ and $AR_{0.35}$ are then applied as artefact reference signals into an adaptive filter (AF).

Figure 8:
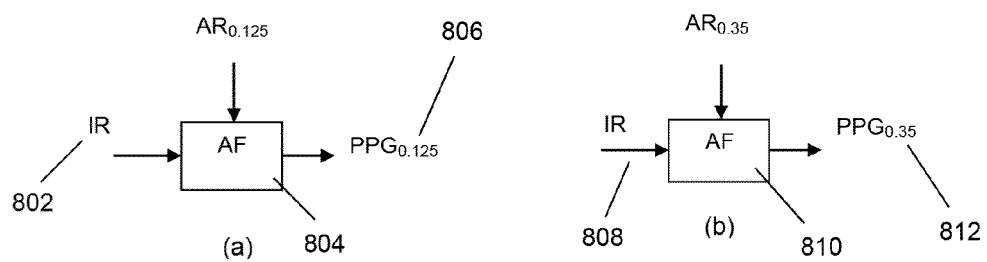
FIG. 8(a) is a diagram showing an artefact signal $AR_{0.125}$ being applied into an adaptive filter in an example embodiment.
FIG. 8(b) is a diagram showing an artefact signal $AR_{0.35}$ being applied into an adaptive filter in an example embodiment.

FIG. 8(a) is a diagram showing an artefact signal $AR_{0.125}$ being applied into an adaptive filter in the example embodiment. The corresponding IR PPG signal 802 is also applied to the adaptive filter 804. It has been recognised that IR signals contain lesser artefact components as compared to R signals. Compare FIG. 6. Thus, in the example embodiment, the IR signal is used for artefact removal. The output is an output PPG signal $PPG_{0.125}$ 806.

FIG. 8(b) is a diagram showing an artefact signal $AR_{0.35}$ being applied into an adaptive filter in the example embodiment. The corresponding IR PPG signal 808 is also applied to the adaptive filter 810. The output is an output PPG signal $PPG_{0.35}$ 812.

In the binary search approach, the output PPG signals (with artefacts removed), $PPG_{0.125}$ and $PPG_{0.35}$ are checked with measured parameters such as, but not limited to, minimum standard deviation (STD), i.e. the averaged standard deviation of maximum peak points and minimum peak points or cross-correlation of two separated segments, e.g. a ten-second output PPG signal is separated into two five-second segments and cross-correlated.

Figure 9:
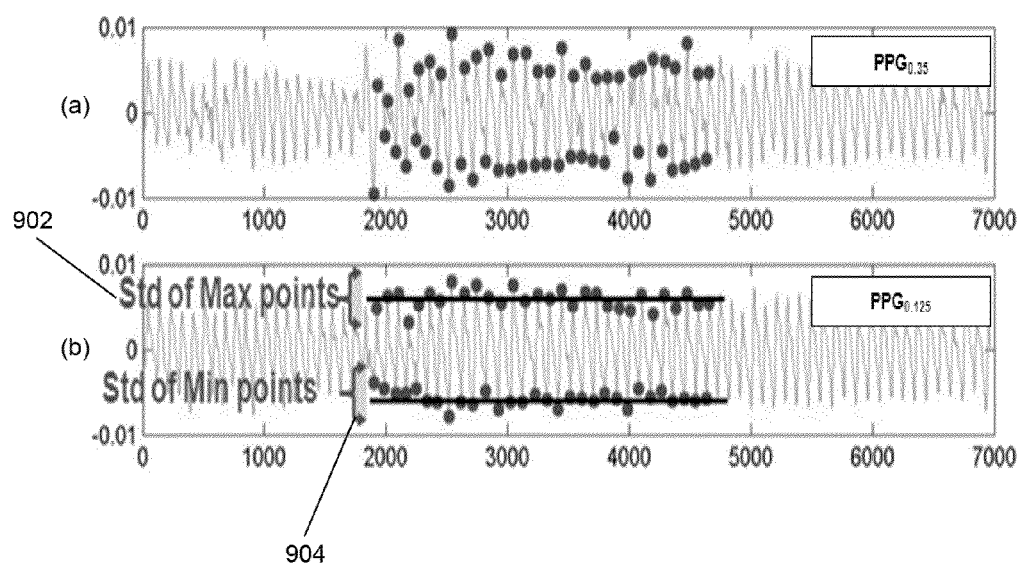
FIG. 9(a) shows an artefact-removed PPG signal $PPG_{0.35}$ in an example embodiment.
FIG. 9(b) shows an artefact-removed PPG signal $PPG_{0.125}$ in an example embodiment.

FIG. 9(a) shows an artefact-removed PPG signal $PPG_{0.35}$ in the example embodiment. FIG. 9(b) shows an artefact-removed PPG signal $PPG_{0.125}$ in the example embodiment. From FIG. 9(b), a standard deviation 902 of the maximum peak points is obtained. A standard deviation 904 of the minimum peak points is also obtained.

Figure 10:
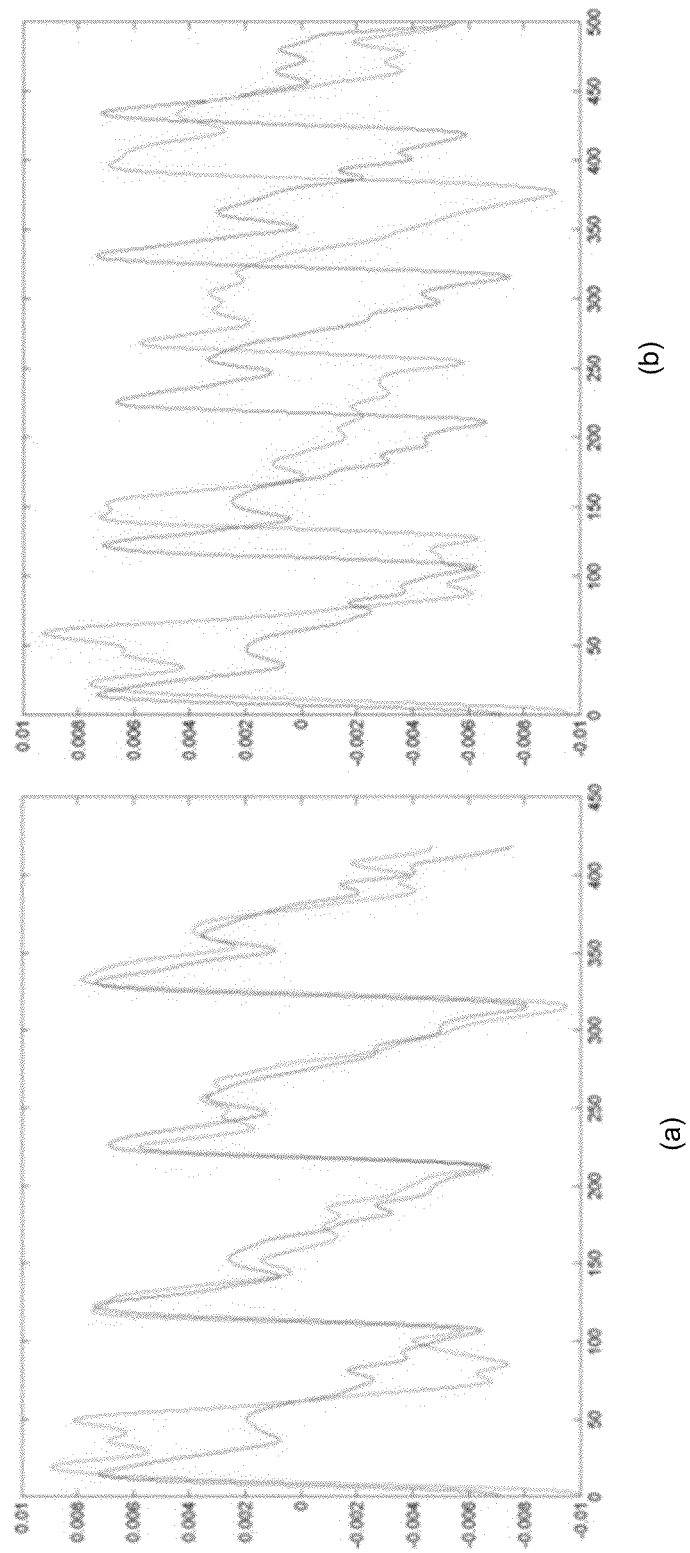
FIG. 10 shows a cross-correlation of two separated segments in an example embodiment.

FIG. 10(a) shows a cross-correlation of two separated segments of an output PPG signal in the example embodiment whereby there are minimum artefacts. FIG. 10(b) shows a cross-correlation of two separated segments of an output PPG signal in the example embodiment whereby there are more artefacts than FIG. 10(a). Each figure shows two segments of an output PPG signal (e.g. $PPG_{0.125}$ 806 or $PPG_{0.35}$ 812) overlaid over each other. If artefacts are totally removed, the overlaid two segments are determined to have perfect correlation. That is, if the output PPG signal (e.g. $PPG_{0.125}$ 806 or $PPG_{0.35}$ 812) has no motion artefact, the correlation is high.

In the example embodiment, one of the two parameters i.e. minimum standard deviation and cross-correlation of two separated segments, can be used. If $PPG_{0.125}$ has a lower STD as compared to $PPG_{0.35}$ from FIG. 9, then the $S_{green}$ subspace [from 0 to 0.24] is considered for the next step.

That is, referring to graph 704 of FIG. 7, the $S_{green}$ subspace [from 0 to 0.24] is further divided into two subspaces 706, 708. There are 25 AR signals remaining. A third analysis signal is selected from a first subspace 706 of the $S_{green}$ subspace [e.g. from 0 to 0.12] with the third analysis signal approximately at the centre of the first subspace 706. A fourth analysis signal is selected from a second subspace 708 of the $S_{green}$ subspace [e.g. from 0.13 to 0.24] with the fourth analysis signal approximately at the centre of the second subspace 708. The adaptive filtering process e.g. shown in FIGS. 8(a) and (b) is again carried out with the third and fourth analysis signals. Thereafter, a comparison process e.g. shown in FIGS. 9(a) and (b) or FIGS. 10(a) and (b) are carried out. Thus, a first/second subspace 706,708 of the $S_{green}$ subspace is considered for the next iterative step.

For the next iterative step, at graph 710, the selected first/second subspace of the $S_{green}$ subspace is further divided into two subspaces 712,714. There are about 13 AR signals remaining. A fifth analysis signal is selected from the subspace 712 and a sixth analysis signal is selected from the subspace 714, the fifth and the sixth analysis signals being approximately at the centre of their respective subspaces 712, 714. The adaptive filtering process e.g. shown in FIGS. 8(a) and (b) is again carried out with the fifth and sixth analysis signals. Thereafter, a comparison process e.g. shown in FIGS. 9(a) and (b) or FIGS. 10(a) and (b) are carried out. Thus, a subspace 712,714 is considered for the next iterative step at graph 712 with seventh and eighth analysis signals. The iterations continue until a final two analysis signals are left, for analysis to obtain an optimum AR signal.

That is, based on the above description, the binary search approach iteratively reduces the vector space until no further subspace can be provided, and thus, providing an optimum AR signal.

In this way, the best artefact removed PPG signal with respect to an optimum AR signal and $ratio_{opt}$ is selected for each pair of R and IR PPG signals. With the vector subspace binary search approach, the number of analyzed AR signals for one pair of R and IR PPG signals can be reduced approximately to 12 AR signals (i.e. first analyzed AR signal, second analyzed AR signal, ..., twelfth analyzed AR signal) instead of analyzing all 100 AR signals. For example, from about 50 AR signals, 2 AR signals are analysed. Thereafter, from about 25 AR signals, another 2 AR signals are analysed. Thereafter, from about 13 AR signals, another 2 AR signals are analysed. Thereafter, from about 7 AR signals, another 2 AR signals are analysed. Thereafter, from about 4 AR signals, another 2 AR signals are analysed. The above analaysed AR signals are each selected from the midpoint of a respective subspace. Thereafter, the remaining 2 AR signals are analysed to find the optimum AR signal. Thus, only 12 AR signals, instead of 100, are analysed for each pair of R and IR PPG signals.

Therefore, for all 16 pairs of R and IR PPG signals of FIG. 5, the number of analyzed AR signals can be reduced from 1600 AR signals (i.e. 16 pairs×100 AR signals=1600 AR signals) to approximately 192 AR signals (i.e. 16 pairs×12 AR signals=192 AR signals).

For each pair of R and IR PPG signal, the optimum AR signal is used to obtain a candidate PPG signal. Therefore, for 16 pairs of R and IR PPG signals, 16 candidate PPG signals are obtained.

From the 16 pairs of R and IR PPG signals of FIG. 5, a best artefact removed PPG output signal is then chosen from the resultant 16 candidate PPG signals. In the example embodiment, this is obtained by using the STD parameter where the output signal with a minimum STD is selected as the best signal. All vital signs (HR, HRV, SpO2) are then computed using the selected signal.

Table 2 below tabulates the STD of an exemplary 16 pairs of R and IR PPG signals experimentally obtained.

TABLE 2

| STD | R1 | R2 | R3 | R4 |
|---|---|---|---|---|
| IR1 | 0.004965 | 0.005491 | 0.004182 | 0.005014 |
| IR2 | 0.005604 | 0.005078 | 0.005198 | 0.005427 |
| IR3 | 0.006414 | 0.006335 | 0.006024 | 0.006799 |
| IR4 | 0.006238 | 0.006474 | 0.006242 | 0.004723 |

Thus, the output signal with the minimum STD of 0.004182 is selected as the best signal.

Having considered usage of a PD array to assist in artefact removal, the inventors have also recognised that adding pressure to a measurement site via one or more of the photodetectors of the array can improve measurements.

Figure 11:
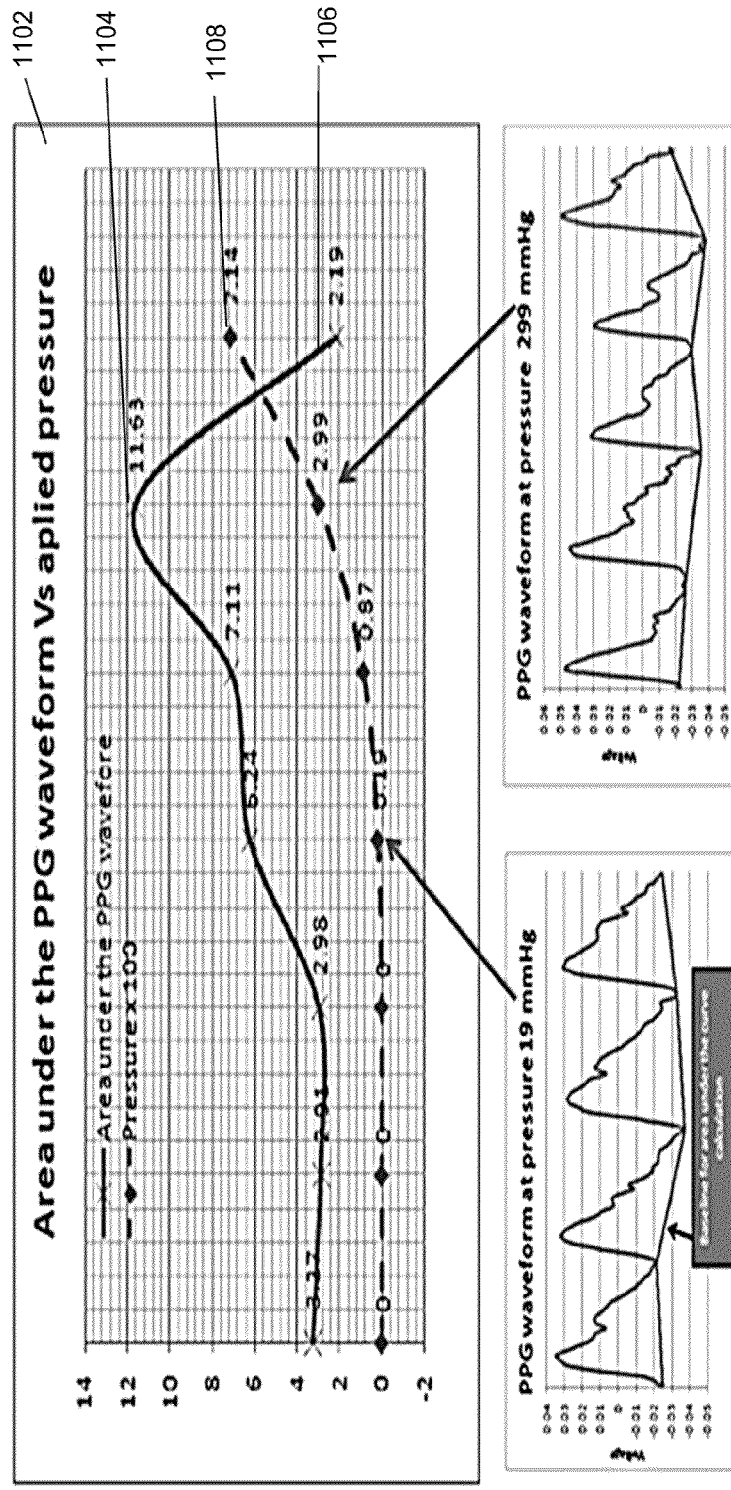
FIG. 11 is a graph illustrating a PPG signal variation under applied pressure in an example embodiment.

FIG. 11 is a graph 1102 illustrating a PPG signal variation under applied pressure in an example embodiment. A photodetector is used to measure a PPG signal. The plot 1106 denotes the area under the PPG signal waveform. The plot 1108 denotes the applied pressure. The graph 1102 shows that when applied pressure on the measurement site by the photodetector during the PPG measurement is increased, the amplitude of the PPG signal is increased. It can be observed that under a certain pressure, the amplitude of the PPG signal reaches its maximum 1104 and beyond that pressure, the amplitude of the obtained PPG signal decreases again. The pressure/force at that certain point is called the optimum pressure/force and if that force is maintained during PPG measurement, the PPG signal can be maintained at its optimum condition. To apply pressure on the measurement sites, any kind force/pressure mechanism can be used such as, but not limited to, air pressure, or mechanical ways of tightening the LED and PD housings.

Figure 12:
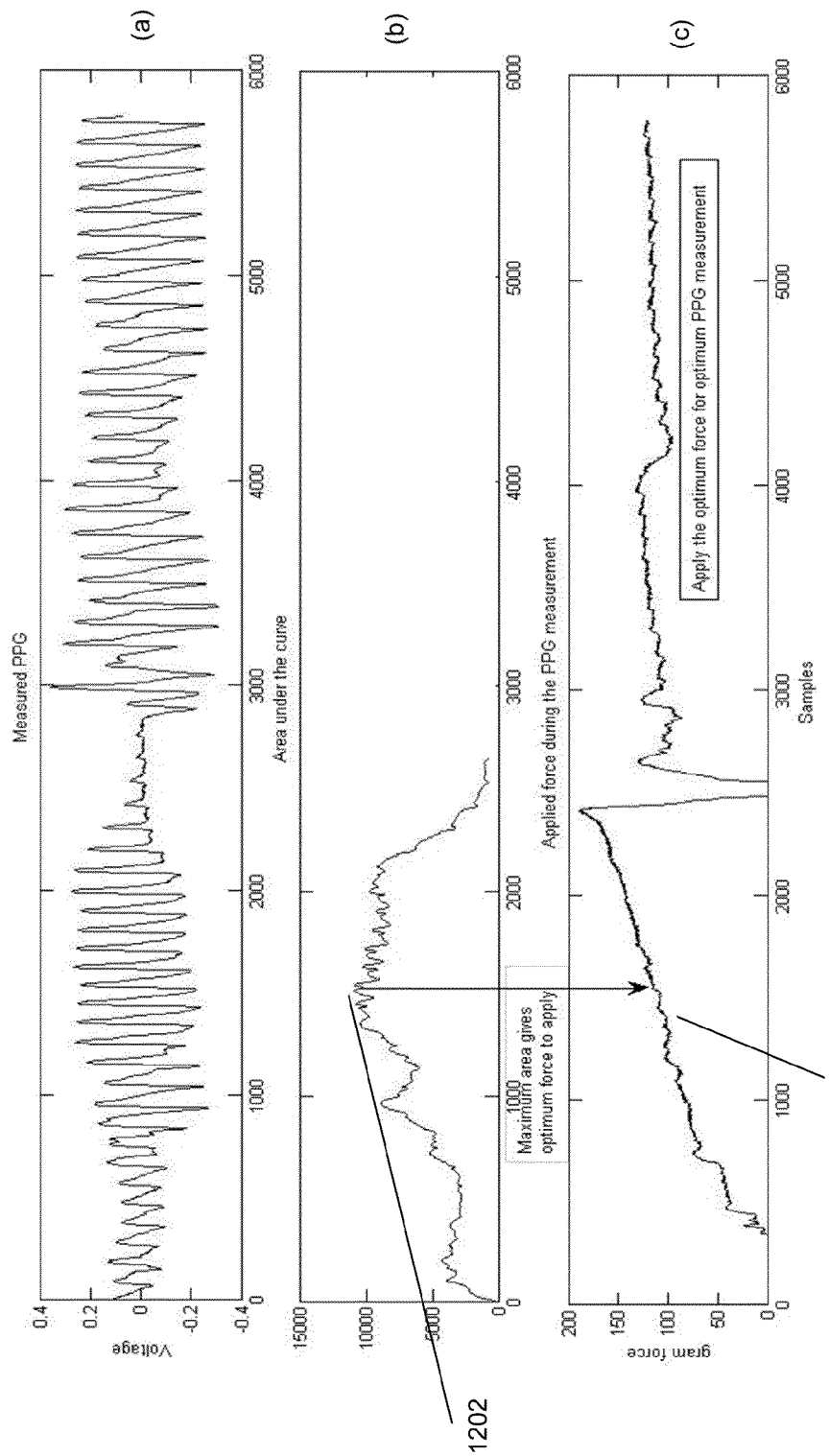
FIG. 12(a) is a waveform of a measured optimum PPG signal in an example embodiment.
FIG. 12(b) is a graph showing the area under the waveform of FIG. 12(a).
FIG. 12(c) is a graph showing applied pressure on a measurement site in an example embodiment.

FIG. 12(a) is a waveform of a measured optimum PPG signal in an example embodiment. FIG. 12(b) is a graph showing the area under the waveform of FIG. 12(a). FIG. 12(c) is a graph showing the applied pressure on the measurement site. From FIG. 12(b), the maximum area under the curve at 1202 is identified and the corresponding pressure at 1204 is also identified. The pressure at 1204 is the optimum pressure/force to be maintained during PPG measurement.

Figure 13:
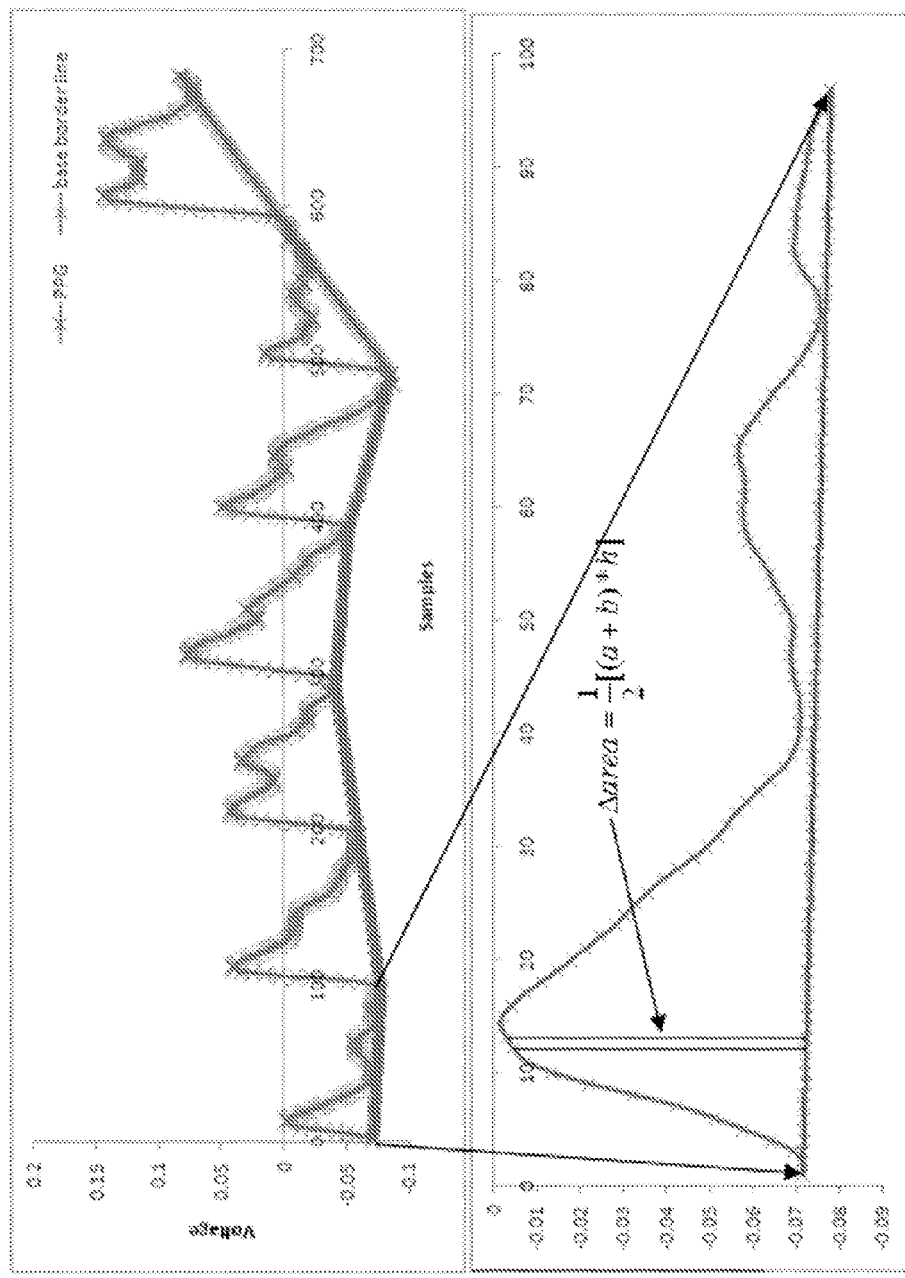
FIG. 13 shows schematically the trapezoidal rule computation for area under the curve.

As described, the amplitude of the PPG signal is measured using area under the curve. Area under the curve can be computed using the trapezoidal rule. The trapezoidal rule computation for area under the curve is shown schematically in FIG. 13.

The inventors have recognized that by using the trapezoidal rule, a significant number of computation steps would be required. Therefore, a light weight method is proposed as an alternative to compute the area under the curve.

Figure 14:
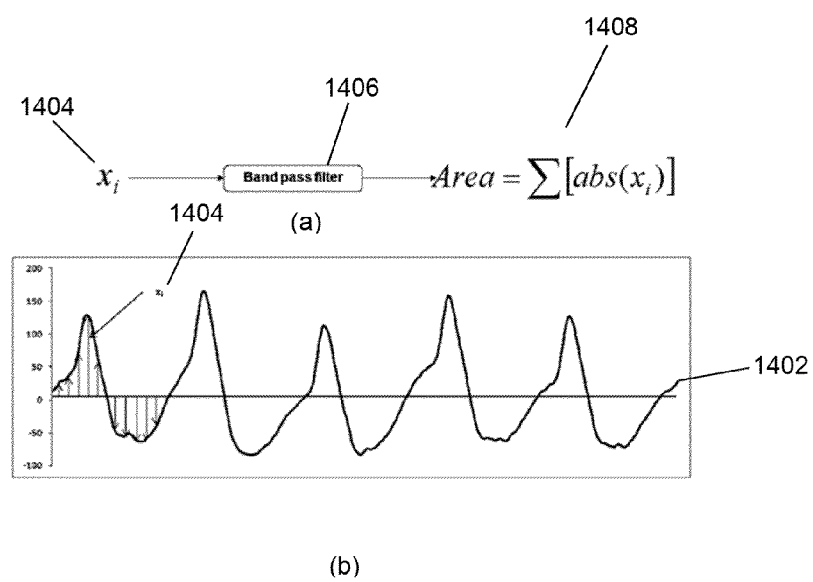
FIG. 14(a) is a schematic diagram illustrating a light weight computation method to compute area under a curve in an example embodiment.
FIG. 14(b) shows a PPG signal curve in an example embodiment.

FIG. 14(a) is a schematic diagram illustrating a light weight computation method to compute area under a curve in an example embodiment. FIG. 14(b) shows a PPG signal curve in an example embodiment. The PPG signal curve 1402 is sampled to provide samples $X_i$ 1404. Each PPG signal sample $X_i$ 1404 is filtered using a band pass filter 1406 to e.g. remove DC components of the signal. The approximate area under the curve of the PPG signal curve 1402 is computed using a summation 1408 of the absolute values of the samples. This method is conceptually similar as using the trapezoidal rule, but is based on the assumption that when the trapezium becomes infinitesimally small, the trapezium becomes a single straight line. With this method, computational steps can be avoided. In addition, the method is relatively simple and can minimize errors in computation.

Returning to the subject of applying pressure/force, in the example embodiment, optimum force is applied by manually tightening the sensor/photodetector housing or the measurement device 102 (FIG. 1).

Figure 15:
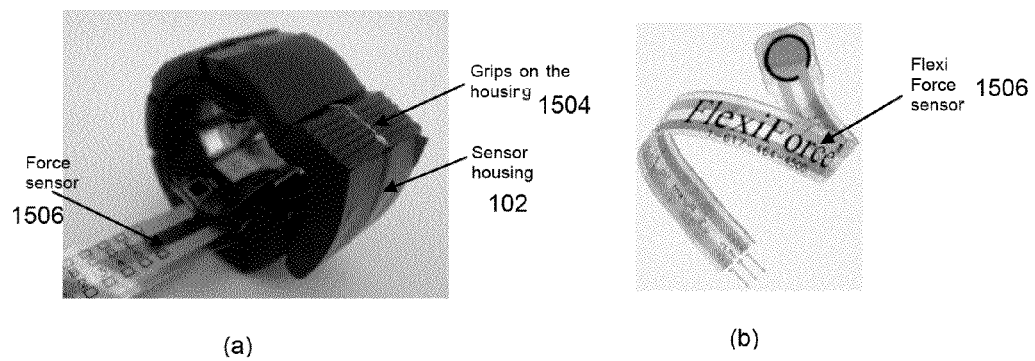
FIG. 15(a) is a picture showing a sensor housing in an example embodiment.
FIG. 15(b) shows a flexi force sensor used in an example embodiment.

FIG. 15(a) is a picture showing a sensor housing in an example embodiment. FIG. 15(b) shows a flexi force sensor used in an example embodiment. The housing 102 can be tightened as it is provided with grips 1504 that allow the interior size of the housing 102 to be incrementally adjusted. As the housing 102 is placed around a subject's finger 104 (FIG. 1), adjusting the interior size corresponds to a change in the pressure applied on the various measurement sites by the finger 104 (FIG. 1). The pressure can be detected using the force sensor 1506. Prior to actual measurement, the optimum pressure can be determined by means of a calibration phase where at each step, the area under the curve can be computed. Refer to FIG. 12(b). The interior size of the housing 102 which produces the maximum area under the curve is selected for the optimum pressure/force.

In an alternative example embodiment, the above-mentioned calibration phase may be automated using an automatic sizing component such that the interior size of the housing 102 is automatically adjusted to tighten in a step wise manner until all possible sizes are sampled. Thereafter, the optimum size is automatically determined to provide the largest area under the curve. The housing 102 is then adjusted to the determined optimum size. An example of the automatic sizing component comprises a controller coupled to the housing for controlling an air pump and a solenoid. The air pump and solenoid are in turn connected to the housing. The housing is made inflatable such that the air pump and solenoid can pump air into or remove air from the housing to respectively tighten or loosen the housing.

In another example embodiment, a low power wireless transceiver using wireless communication protocol can be implemented at the measurement device. The wireless communication protocol can be, for example, Bluetooth technology or ZigBee.

Figure 16:
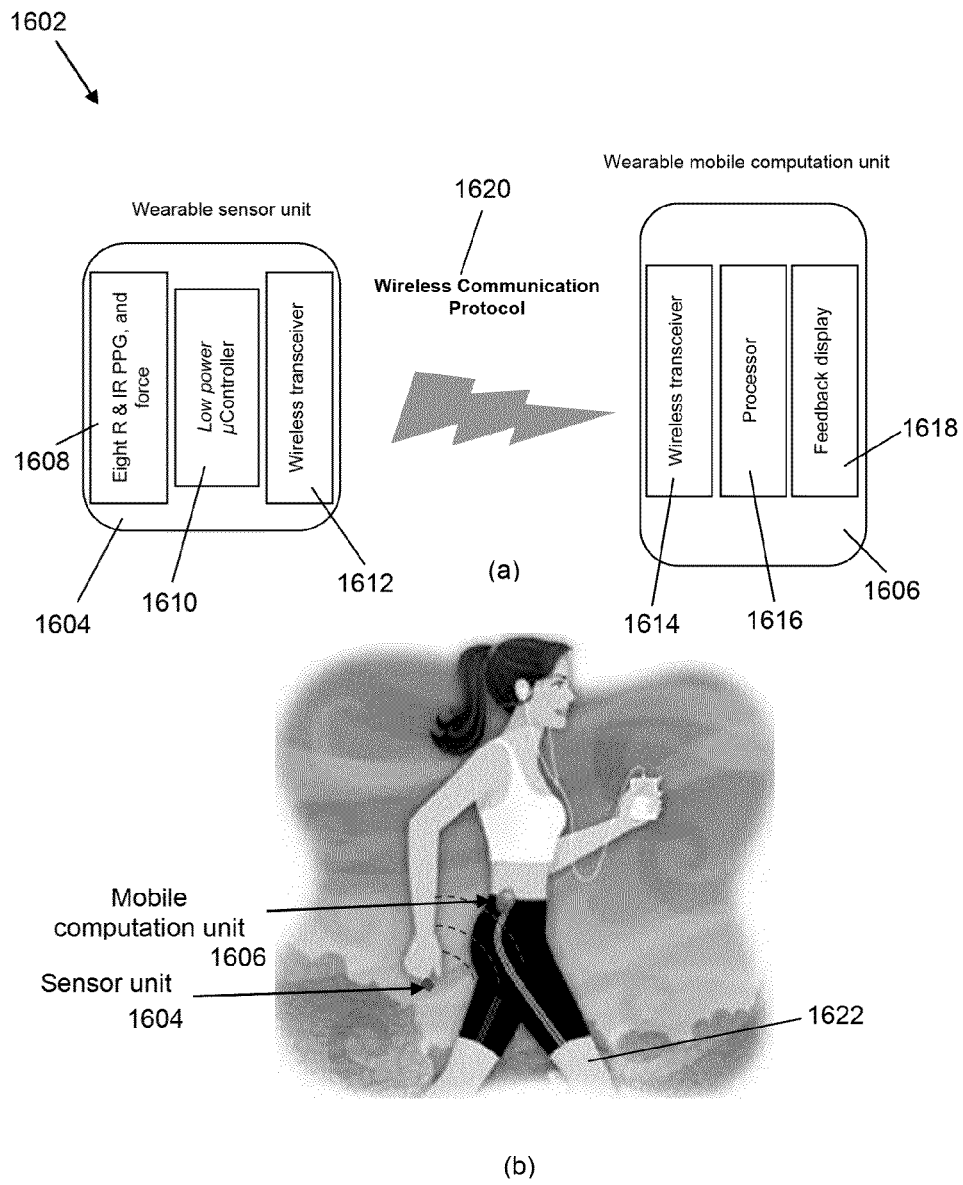
FIG. 16(a) is a schematic diagram showing a measurement system in an example embodiment.
FIG. 16(b) is a picture showing a subject wearing a sensor unit and a mobile computation unit in an example embodiment.

FIG. 16(a) is a schematic diagram showing a measurement system in an example embodiment. The system 1602 comprises a wearable sensor unit 1604 and a wearable mobile computation unit 1606. The wearable sensor unit 164 comprises a four PD array measurement element 1608, a low power microcontroller 1610 and a wireless transceiver 1612. The computation unit 1606 comprises a wireless transceiver 1614, a processor 1616 and a feedback display 1618. The transceivers 1612, 1614 communicate using a wireless communication protocol 1620. The measured R and IR PPG signals from the measurement element 1608 can be sent to the remote wearable mobile computation unit for further processing. In the example embodiment, the transceiver 1612 at the sensor unit 1604 transmits data to the computation unit 1606.

FIG. 16(b) is a picture showing a subject wearing the sensor unit 1604 and the mobile computation unit 1606 in the example embodiment. In the example embodiment, the sensor unit 1604 is worn at the subject's finger and the mobile computation unit 1606 is remote from the sensor unit 1604. The mobile computation unit 1606 can, for example, be worn at a belt or an arm band.

Figure 17:
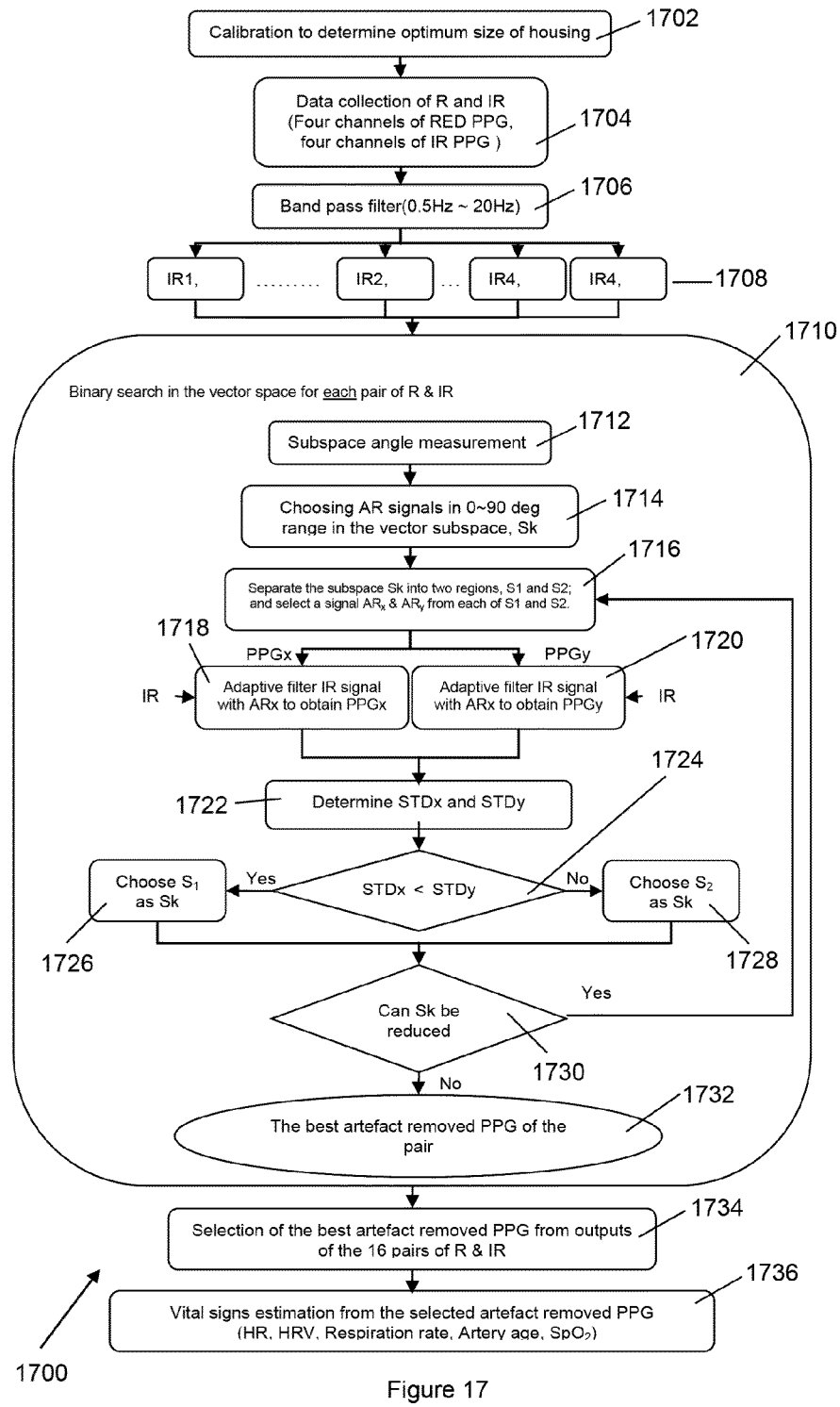
FIG. 17 is a flowchart illustrating steps for using a measurement system in an example embodiment.

FIG. 17 is a flowchart 1700 illustrating steps for using the measurement system 1602 in the example embodiment. The steps taken by the mobile computation unit is from steps 1706 onwards. At step 1702, a calibration phase is carried out to determine an optimum interior size of the sensor housing. At step 1704, data collection of red (R) and infrared red (IR) PPG signals is performed. At step 1706, the data collected is filtered in a range of about 0.5 Hz to about 20 Hz using a band pass filter. At step 1708, 16 pairs of R and IR signals are formed. At step 1710, a binary search in a vector space for each pair of R and IR PPG signals is performed. For a current pair of R and IR PPG signals, at step 1712, a subspace angle measurement is performed. At step 1714, artefact reference (AR) signals in 0~90 degrees range in the vector subspace Sk are chosen. At step 1716, the subspace Sk is separated into two regions S1 and S2. A signal $AR_x$ is selected from S1 and a signal $AR_y$ is selected from S2. At step 1718, an adaptive filter is used to filter the current IR PPG signal with $AR_x$ to obtain artefact removed PPG signal $PPG_x$. At step 1720, an adaptive filter is used to filter the current IR PPG signal with $AR_y$ to obtain artefact removed PPG signal $PPG_y$. At step 1722, a minimum standard deviation $STD_x$ (or averaged standard deviation of the maximum peak points and of the minimum peak points) of $PPG_x$ is obtained. A minimum standard deviation $STD_y$ (or averaged standard deviation of the maximum peak points and of the minimum peak points) of $PPG_y$ is also obtained. At step 1724, it is determined whether $STD_x$ is less than $STD_y$. If $STD_x$ is lesser, at step 1726, S1 is chosen as SK. Otherwise, if $STD_x$ is greater than $STD_y$, at step 1728, S2 is chosen as SK. At step 1730, it is determined whether the chosen Sk can be further reduced. It is appreciated that if the number of remaining AR signals is less than or equal to three, the subspace Sk cannot be reduced further. If yes, the processing loops back to step 1716. If not, the best artefact removed PPG signal of the current pair of R and IR signals is obtained. At step 1734, after computation of the 16 pairs of R and IR signals to provide 16 candidate PPG signals, a selection of the best artefact removed PPG signal from the 16 pairs is performed. At step 1736, vital signs estimation can be performed from the selected PPG signal of step 1734. The vital signs can include heart rate HR, heart rate variation HRV, respiration rate, artery age, $SpO_2$ etc.

For example, HR is obtained by counting the number of PPG peaks at each time segment. If a segment is 15 seconds long, HR is the number of detected peaks multiplied by 4 and resulted in number of peaks per minute. HRV is the standard deviation of those detected peak values. Then, $SpO_2$ is determined using the following equation.

$$SpO_2 = \frac{ratio_{opt} \varepsilon_{Hb}(\lambda_{IR}) - \varepsilon_{Hb}(\lambda_R)}{ratio_{opt}[\varepsilon_{Hb}(\lambda_{IR}) - \varepsilon_{Hbo}(\lambda_{IR})] + \varepsilon_{Hbo}(\lambda_R) - \varepsilon_{Hb}(\lambda_R)}$$

where $\varepsilon_{Hb}$ and $\varepsilon_{Hbo}$ are extinction coefficients of R and IR wavelengths and $\lambda_{IR}$ and $\lambda_R$ are the wavelengths of the infrared and red light sources respectively. In an example, extinction coefficients are
$\varepsilon_{Hb}(\lambda_R)$=820(Mol·cm)⁻, $\varepsilon_{Hb}(\lambda_{IR})$–100(Mol·cm)$^{-1}$, $\varepsilon_{Hbo}(\lambda_R)$=100(Mol·cm)$^{-1}$, $\varepsilon_{Hbo}(\lambda_{IR})$=260(Mol·cm)$^{-1}$
and $\lambda_{IR}$ and $\lambda_R$ are about 900 nm and about 640 nm respectively.

Referring to FIG. 1(c), it is described that the LED is positioned on the side of the finger 104. The following description describes why it is desirable or preferred to position the LED on the side of the finger 104. This optimized position can minimize motion artefacts.

Figure 18:
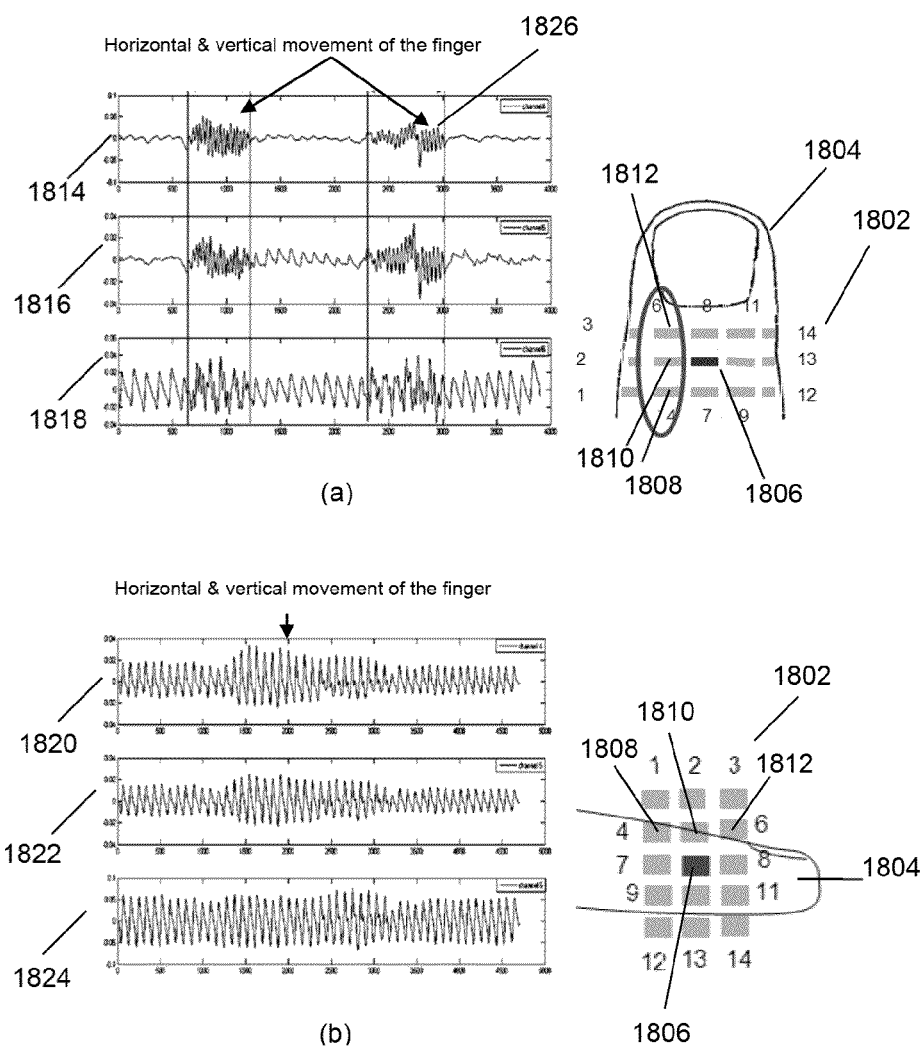
FIG. 18(a) shows a fourteen photo-detector (PD) array wrapped around a finger in an example embodiment.
FIG. 18(b) shows a fourteen PD array wrapped around a finger in an example embodiment.

FIG. 18(a) shows a fourteen PD array 1802 wrapped around a finger 1804 in an example embodiment. The LED 1806 is disposed on the top of the finger 1804. The readings of photodetectors 4, 5 and 6 (numerals 1808, 1810, 1812 respectively) are taken. The readings are respectively shown at 1814, 1816, 1818.

FIG. 18(b) shows the fourteen PD array 1802 wrapped around the finger 1804 in an example embodiment. The LED 1806 is disposed on the side of the finger 1804. The readings of photodetectors 4, 5 and 6 (numerals 1808, 1810, 1812 respectively) are taken. The readings are respectively shown at 1820, 1822, 1824.

As shown in readings 1820, 1822, 1824, when the LED 1806 is located at the side of the finger 1804, the PPG signals are observed to have less motion artefacts than when the LED 1806 is located on top of the finger 1804. From readings 1814, 1816, 1818, significant motion artefacts can be observed at e.g. 1826.

In an effort to validate a motion artefact removed PPG signal, an electrocardiogram (ECG) signal is obtained for the validation. The artefact removed PPG signal and the ECG signal are captured at the same time.

Figure 19:
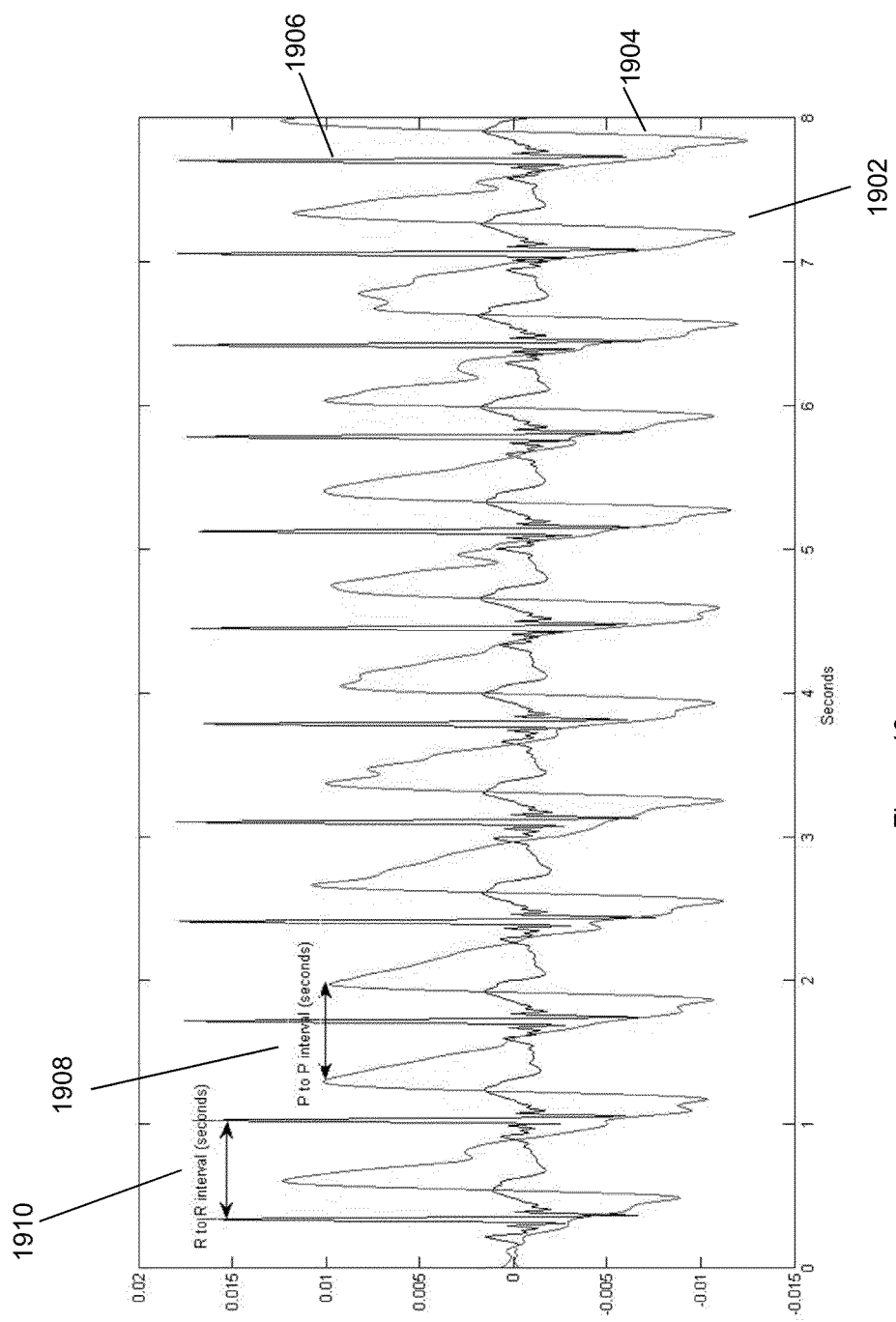
FIG. 19 is a graph showing a PPG signal and an electrocardiogram (ECG) signal in an example embodiment.

FIG. 19 is a graph 1902 showing the PPG signal 1904 and the ECG signal 1906 in the example embodiment. Peak to peak intervals (PtP) e.g. 1908 from the PPG signal 1904 and R peak to the next R peak intervals (RtR) e.g. 1910 of the ECG signal 1906 are used as parameters in validation.

To obtain the artefact removed PPG signal, a four PD array is used in the example embodiment.

Figure 20:
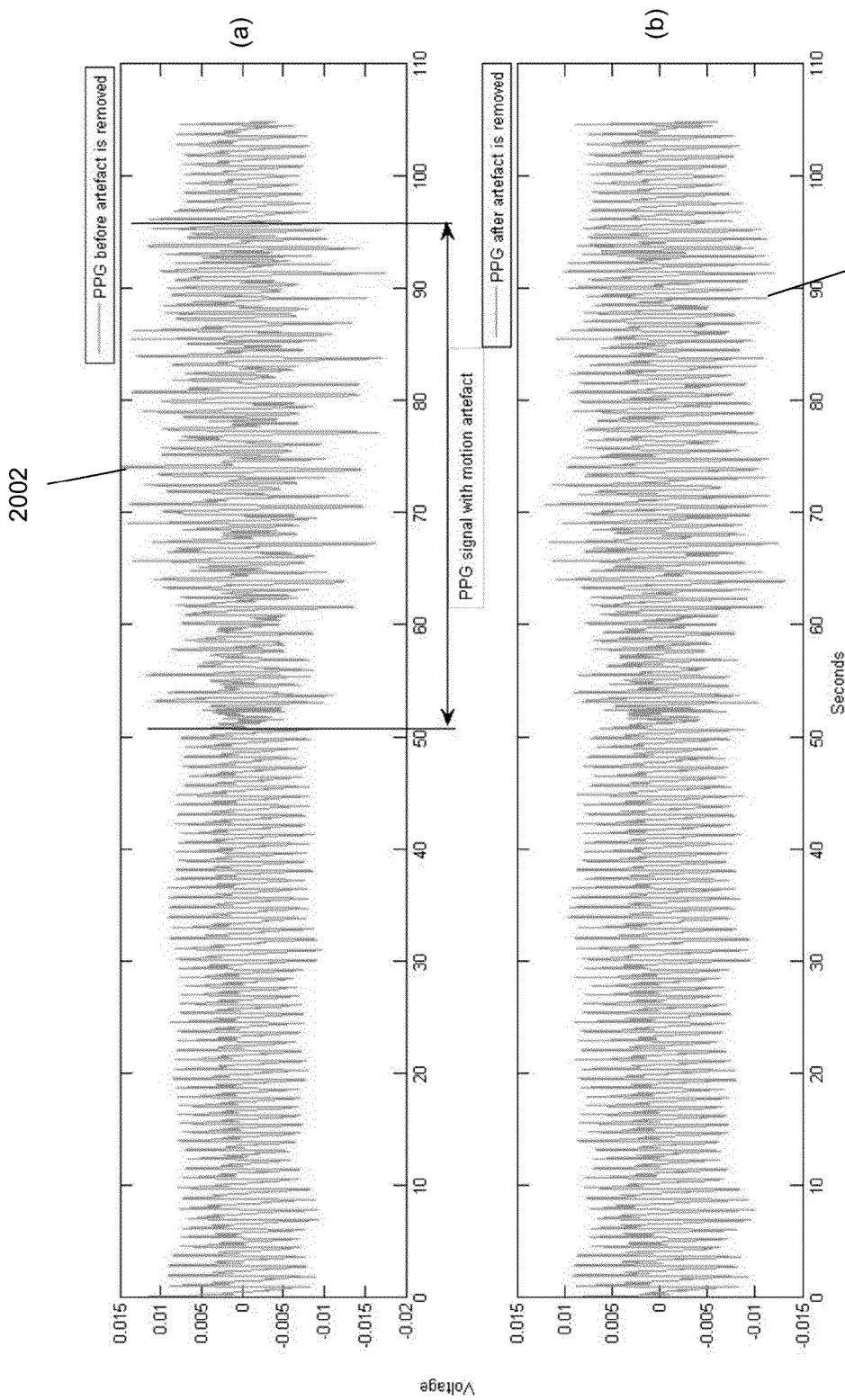
FIG. 20(a) shows a PPG signal obtained from a subject while walking in an example embodiment.
FIG. 20(b) shows an artefact removed PPG signal in an example embodiment.

FIG. 20(a) shows a PPG signal obtained from a subject while walking in the example embodiment. The PPG signal contains motion artefacts at e.g. region 2002. FIG. 20(b) shows an artefact removed PPG signal 2004 in the example embodiment. The best artefact removed PPG signal is observed at e.g. IR1 & R3 pair.

Figure 21:
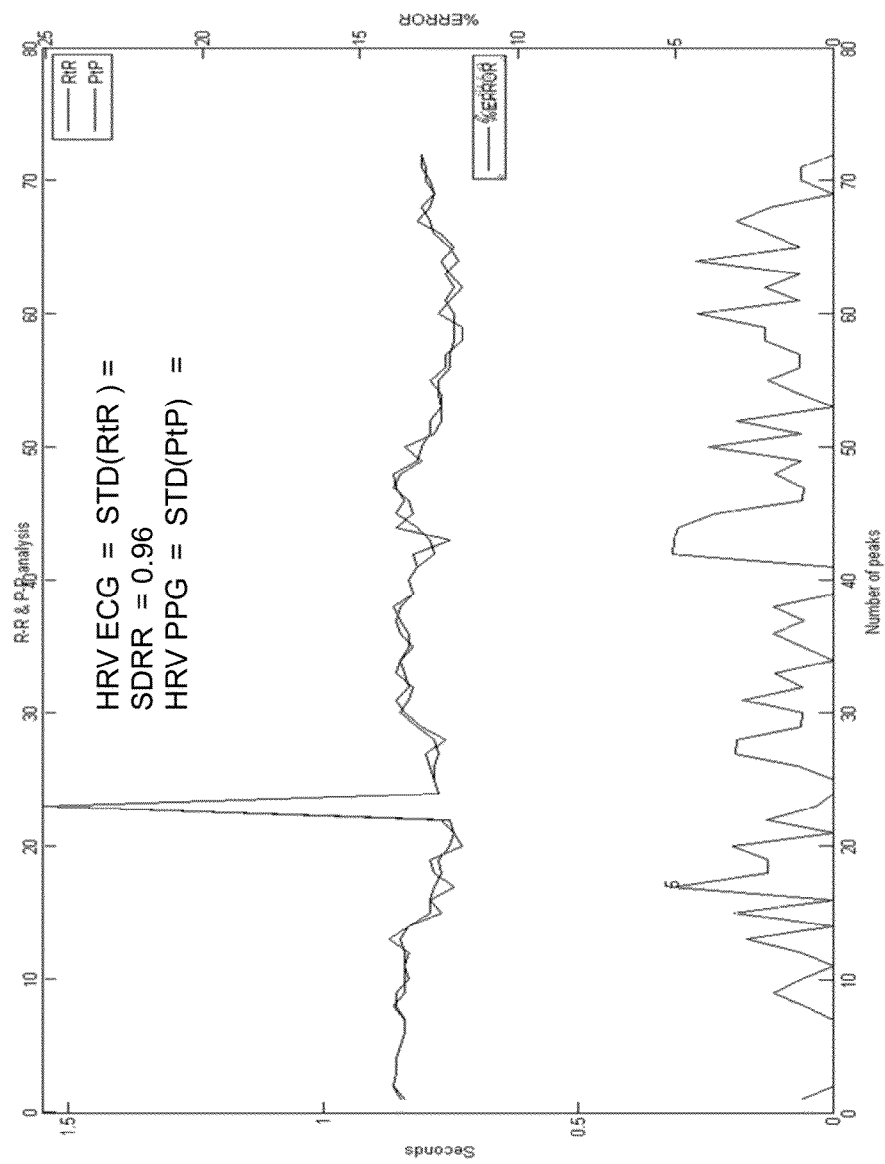
FIG. 21 shows Peak to peak intervals (PtP) and R peak to the next R peak intervals (RtR) intervals of the signals of FIG. 19.

FIG. 21 shows the PtP and RtR intervals e.g. 1908, 1910 of FIG. 19. The standard deviation of the RtR interval (SDRR) and that of the PtP interval (SDPP) are approximately the same, i.e. about 0.97. The % error value for each PtP and RtR point is computed as $$\% \text{ Error} = \frac{\text{abs}(RtR - PtP)}{RtR} * 100.$$

Table 3 shows the summation of %error values for each pair of R and IR PPG signal.

TABLE 3

| Sum of % error | R1 | R2 | R3 | R4 |
| --- | --- | --- | --- | --- |
| IR1 | 857.6251 | 861.3242 | 218.0814 | 764.8914 |
| IR2 | 1364.032 | 1032.259 | 1268.618 | 1094.086 |
| IR3 | 1610.903 | 1822.743 | 1953.654 | 1851.95 |
| IR4 | 1375.194 | 1399.331 | 1201.4 | 980.2152 |

It can be observed that the minimum error happened at the IR1&R3 pair, i.e. having an error value of about 218. The second lowest error happened at the IR1&R4 pair.

Figure 22:
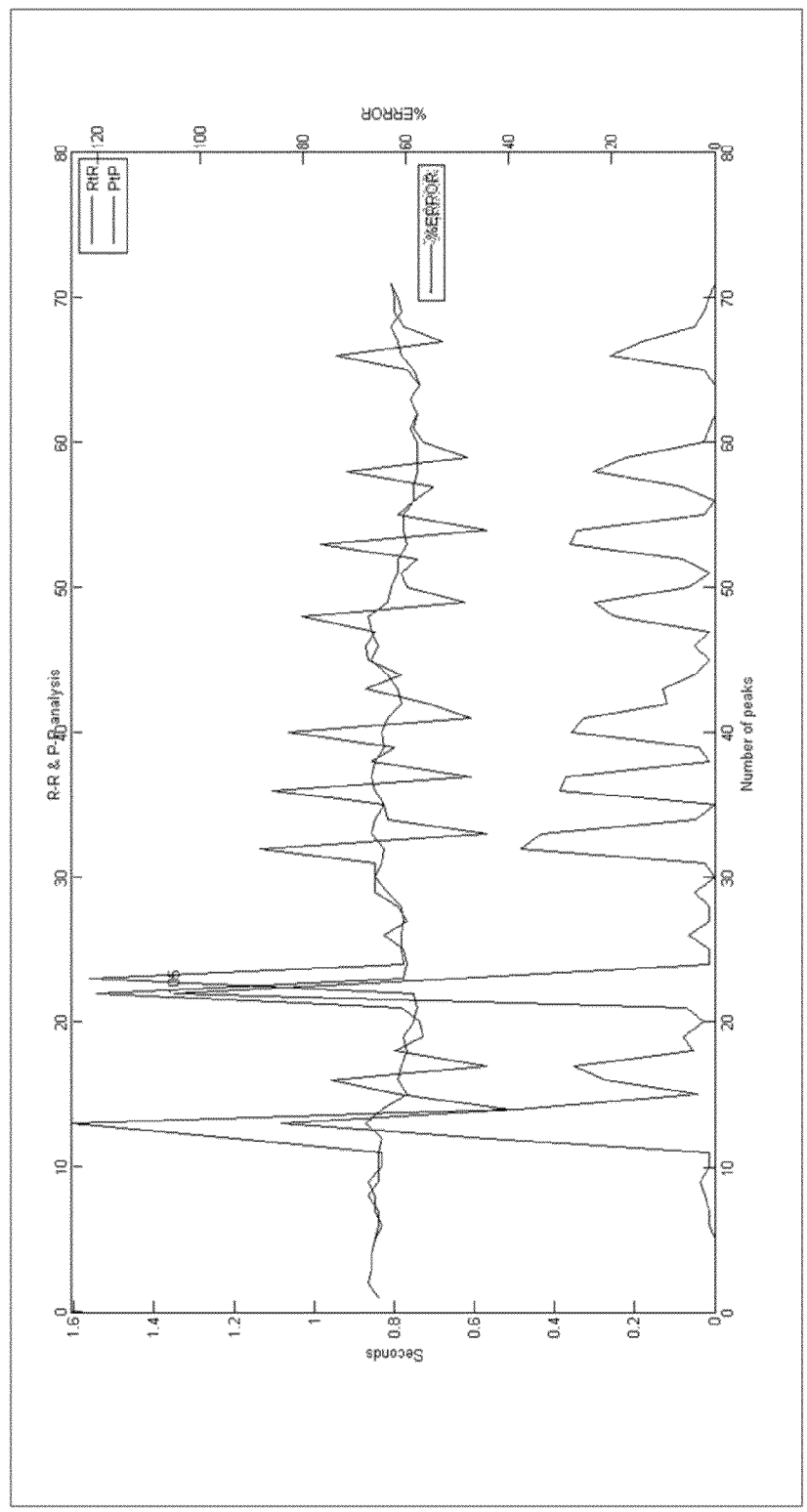
FIG. 22 shows PtP and RtR intervals of a second minimum error pair in an example embodiment.

FIG. 22 shows the PtP and RtR intervals of the second minimum error pair in the example embodiment. The result can be used for comparison against FIG. 21. That is, FIG. 21 shows a very close correlation in the PtP and RtR curves of the ECG and PPG data. Thus, it can be concluded that the data of FIG. 21 has low errors. In contrast, FIG. 22 shows relatively more errors than FIG. 21 as a lower correlation is achieved.

An advantage of using a PD array can be seen clearly by comparing FIG. 22 and FIG. 21. If a single PD is used, the result would be one of the pairs on a diagonal of Table 3 (i.e. IR1&R1, IR2&R2, IR3&R3 or IR4&R4). The optimum result occurring at the IR1&R3 pair cannot be achieved by a single PD.

In alternative embodiments, the number of PDs may be varied. For example, FIG. 23 shows a picture of a nine-PD array and FIG. 24 shows a picture of a fourteen-PD array. With more PDs, a larger surface area of a finger can be covered, and the accuracy of readings can be improved.

Figure 25:
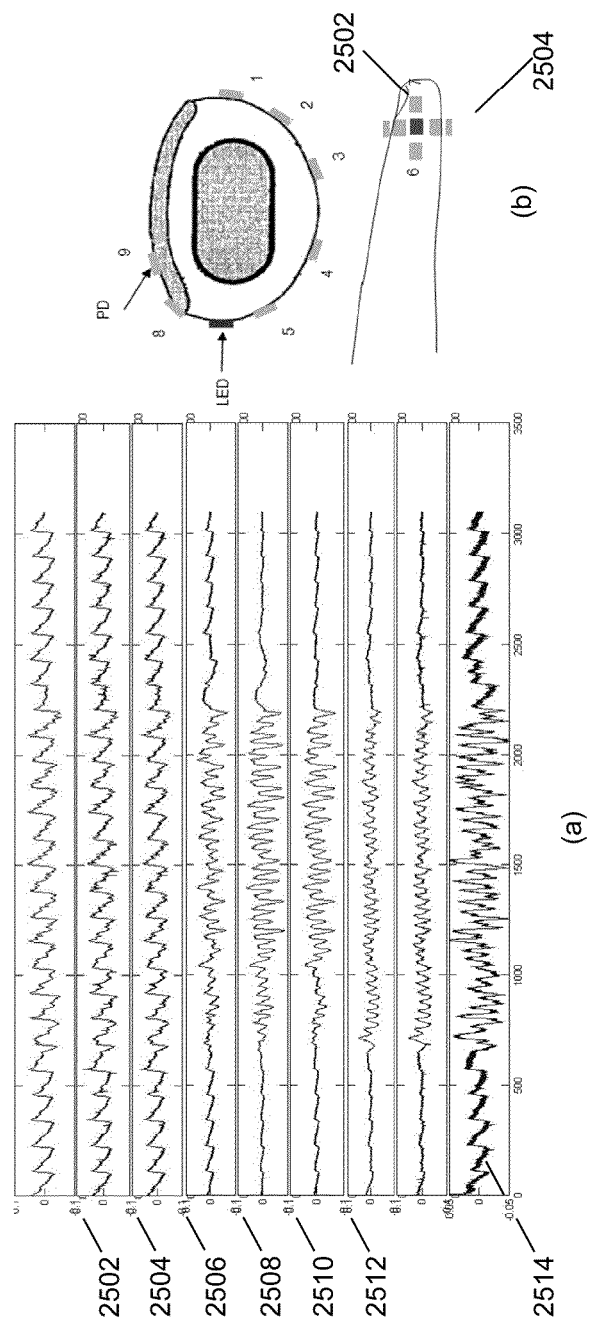
FIG. 25(a) shows infrared red (IR) PPG signals obtained from a nine-PD array in an example embodiment.
FIG. 25(b) shows schematically a nine-PD array attached to a finger in an example embodiment.

FIG. 25(a) shows IR PPG signals obtained from a nine-PD array in an example embodiment. FIG. 25(b) shows schematically the nine-PD array 2502 attached to a finger 2504. From FIG. 25(a), PD1, PD2 and PD3 appear to produce good PPG waveforms at numerals 2502, 2504, 2506 respectively. PD5 and PD6 produce good noise reference signals at numerals 2510, 2512 respectively. PD4, PD9 on the other hand produce some combination of both noise reference and PPG signals at numerals 2508, 2514 respectively. As can be observed, the magnitude of artefacts or noise varies with respect to the location of a PD. Thus, by taking advantage of a PD array, an artefact removed PPG signal can be obtained that is more optimum and accurate than that obtained from using a single PD.

The inventors have recognised that by increasing the number of PDs, the amount of computation and cost is increased as well. In consideration of the cost and the computation, the inventors have recognised that a four-PD array (compare FIG. 1(a)) is preferred as it provides the best performance over cost.

Furthermore, by using the algorithm based on vector subspace approach, the number of analyzed data for a four-PD array is reduced from 16 pairs×100=1600 artefact reference (AR) signals to approximately 192 signals, i.e. 16 pairs×12 AR signals=192 AR signals.

Figure 26:
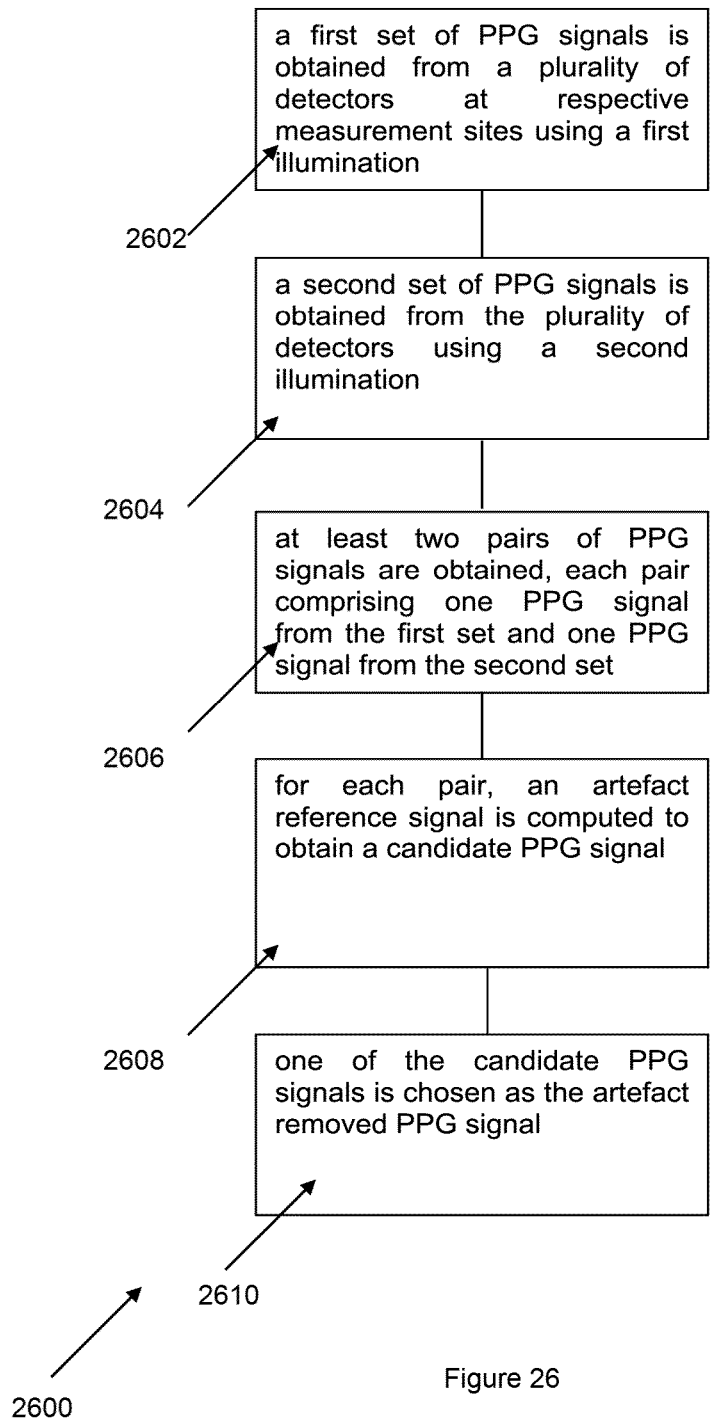
FIG. 26 is a schematic flowchart for illustrating a method of measuring an artefact removed photoplethysmographic (PPG) signal in an example embodiment.

FIG. 26 is a schematic flowchart 2600 for illustrating a method of measuring an artefact removed photoplethysmographic (PPG) signal in an example embodiment. At step 2602, a first set of PPG signals is obtained from a plurality of detectors at respective measurement sites using a first illumination. At step 2604, a second set of PPG signals is obtained from the plurality of detectors using a second illumination. At step 2606, at least two pairs of PPG signals are obtained, each pair comprising one PPG signal from the first set and one PPG signal from the second set. At step 2608, for each pair, an artefact reference signal is computed to obtain a candidate PPG signal. At step 2610, one of the candidate PPG signals is chosen as the artefact removed PPG signal.

In the above described example embodiments, a two step approach is taken for PPG signal motion artefact removal. It has been recognised that measured PPG signals contain desired components and undesired components (e.g. noise, motion artefact etc.). The two step approach comprises artefact minimization and artefact removal. In the above described example embodiments, a multi-photo detector (or multi-PD array) is used. An optimum force can be applied during PPG signal measurement. It has been recognised that a PPG signal obtained with optimum force/pressure can provide distinct features/characteristics at desired components and can minimise undesired PPG signal components. In the above described example embodiments, any type force/pressure mechanism can be used to apply the force/pressure such as, but not limited to, air pressure, mechanical ways of tightening at the measurement site etc. Further, to improve accuracy, the illumination source e.g. an LED can be optimally positioned and signal processing can be carried out using adaptive filters. The LED can be positioned at a site that minimizes undesired components in the measured PPG signal i.e. positioning the LED for minimum motion artefact. In addition, in the above described example embodiments, to reduce computation steps, a vector subspace approach may be used. The vector subspace algorithm can be used to choose/obtain a reference signal (from a plurality of candidate reference signals) with optimum correlation between the reference signal and undesired components of the PPG signals. It has been recognised that optimum correlation occurs when the reference signal represents the undesired components of the PPG signals.

It will be appreciated by a person skilled in the art that numerous variations and/or modifications may be made to the present invention as shown in the specific embodiments without departing from the spirit or scope of the invention as broadly described. The present embodiments are, therefore, to be considered in all respects to be illustrative and not restrictive.

The invention claimed is:

1. A method of producing an artefact removed photoplethysmographic (PPG) signal, the method comprising:
    obtaining a first set of PPG signals from a plurality of detectors at respective measurement sites using a first illumination;
    obtaining a second set of PPG signals from the plurality of detectors using a second illumination;
    obtaining at least two pairs of PPG signals, each pair comprising one PPG signal from the first set and one PPG signal from the second set;
    computing an artefact reference signal based on the each pair of PPG signals using a vector subspace approach by using, for the pairs of PPG signals, artefact reference signals at an angle of between $$0 \sim \frac{\pi}{2}$$

to a PPG signal in the respective pair of PPG signals in the vector subspace and separating the used artefact reference signals into a plurality of subspaces, further wherein from each of said plurality of subspaces, an artefact reference signal selected at the centre of the respective subspace is applied to a filter with one PPG signal from the first set and one PPG signal from the second set to reduce a vector space of artefact reference signals until an optimum artefact reference signal is identified and applied to the filter with one PPG signal from the first set and one PPG signal from the second set as a result of which a candidate PPG signal is obtained from which the artefact has been removed by the filter;
        choosing one of the candidate PPG signals as the artefact removed PPG signal, wherein the step of choosing one of the candidate PPG signals comprises using one or more parameters to compare the candidate PPG signals; and
        estimating vital signs using the chosen candidate PPG signal.

2. The method as claimed in claim 1, wherein the parameters comprise an averaged standard deviation of maximum peak points and minimum peak points of each candidate PPG signal.

3. The method as claimed in claim 1, wherein the parameters comprise a cross-correlation of two separated segments of each candidate PPG signal.

4. The method as claimed in claim 1, further comprising applying a force at the plurality of detectors such that signal amplitudes of the first set of PPG signals and/or the second set of PPG signals are maximum.

5. The method as claimed in claim 4, comprising computing an area under curve measurement using waveforms of the PPG signals to determine whether the signal amplitudes are maximum.

6. The method as claimed in claim 5, wherein the computing an area under curve measurement comprises sampling each waveform and filtering each sample, further wherein the area under curve measurement is a summation of absolute values of the filtered samples.

7. The method as claimed in claim 1, further comprising providing the first and second illumination using a light emitting diode.

8. The method as claimed in claim 7, wherein the light emitting diode is positioned such that motion artefacts are minimized in the first set of PPG signals and/or the second set of PPG signals.

9. The method as claimed in claim 1, wherein the first illumination is red light and the second illumination is infrared light.

10. A non-transitory computer readable data storage medium having stored thereon computer code means for instructing a processor of a measurement system for measuring an artefact removed photoplethysmographic (PPG) signal to execute a method of measuring an artefact removed PPG signal as claimed in claim 1.

11. A measurement system configured to measure an artefact removed photoplethysmographic (PPG) signal, the system comprising,
    a measurement device comprising a plurality of detectors at respective measurement sites configured to obtain a first set of PPG signals using a first illumination and configured to obtain a second set of PPG signals using a second illumination;
    a computation unit configured to obtain at least two pairs of PPG signals, each pair comprising one PPG signal from the first set and one PPG signal from the second set, and the computation unit being configured to, for each pair, compute an artefact reference signal based on the each pair of PPG signals using a vector subspace approach by using, for the pairs of PPG signals, artefact reference signals at an angle of between $$0 \sim \frac{\pi}{2}$$

to a PPG signal in the respective pair of PPG signals in the vector subspace and separating the used artefact reference signals into a plurality of subspaces, further wherein from each of said plurality of subspaces, an artefact reference signal selected at the centre of the respective subspace is applied to a filter with one PPG signal from the first set and one PPG signal from the second set to reduce a vector space of artefact reference signals until an optimum artefact reference signal is identified and applied to the filter with one PPG signal from the first set and one PPG signal from the second set as a result of which a candidate PPG signal is obtained from which the artefact has been removed by the filter; and
    the computation unit being configured to choose one of the candidate PPG signals as the artefact removed PPG signal, wherein the step of choosing one of the candidate PPG signals comprises using one or more parameters to compare the candidate PPG signals,
wherein the system is configured to estimate vital signs by using use the chosen candidate PPG signal.

12. The system as claimed in claim 11, wherein the parameters comprise an averaged standard deviation of maximum peak points and minimum peak points of each candidate PPG signal.

13. The system as claimed in claim 11, wherein the parameters comprise a cross-correlation of two separated segments of each candidate PPG signal.

14. The system as claimed in claim 11, further comprising a force application means for applying a force at the plurality of detectors such that signal amplitudes of the first set of PPG signals and/or the second set of PPG signals are maximum.

15. The system as claimed in claim 14, wherein the computation unit is configured to compute an area under curve measurement using waveforms of the PPG signals to determine whether the signal amplitudes are maximum.

16. The system as claimed in claim 15, wherein for the computing an area under curve measurement, the computation unit samples each waveform and filters each sample, and further the computation unit computes the area under curve measurement as a summation of absolute values of the filtered samples.

17. The system as claimed in claim 14, further comprising an automatic sizing component to automatically size the measurement device for application to a subject, the automatic sizing component functioning as the force application means.

18. The system as claimed in claim 11, further comprising a light emitting diode configured to provide the first and second illumination.

19. The system as claimed in claim 18, wherein the light emitting diode is positioned such that motion artefacts are minimized in the first set of PPG signals and/or the second set of PPG signals.

20. The system as claimed in claim 11, wherein the first illumination is red light and the second illumination is infrared light.

21. The system as claimed in claim 11, wherein the measurement device and the computation unit each comprise a wireless transceiver to facilitate communication using a wireless communication protocol.

* * * * *